(12) United States Patent
Takeoka et al.

(10) Patent No.: US 7,799,319 B2
(45) Date of Patent: Sep. 21, 2010

(54) METHOD FOR MEASURING SKIN ABSORBABILITY

(75) Inventors: Eriko Takeoka, Kanagawa (JP);
Ryuichi Takamoto, Tokyo (JP); Toshio Yanaki, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 1335 days.

(21) Appl. No.: 11/260,714

(22) Filed: Oct. 27, 2005

(65) Prior Publication Data

US 2006/0062730 A1    Mar. 23, 2006

Related U.S. Application Data

(62) Division of application No. 10/238,520, filed on Sep. 9, 2002, now abandoned, which is a division of application No. 09/697,043, filed on Oct. 27, 2000, now abandoned.

(51) Int. Cl.
*A61K 8/00* (2006.01)
*A61K 8/18* (2006.01)
*A61Q 9/00* (2006.01)
*A61Q 5/00* (2006.01)

(52) U.S. Cl. .................. 424/70.1; 424/9.2; 424/401

(58) Field of Classification Search ................ 424/1.11, 424/1.65, 59, 69, 78.02, 78.03, 78.08, 400, 424/401, 408, 409, 9.1, 9.2, 47, 70.1
See application file for complete search history.

(56) References Cited

FOREIGN PATENT DOCUMENTS

| EP | 0795318 A | | 9/1997 |
|---|---|---|---|
| EP | 0811370 A | | 12/1997 |
| EP | 0823250 A | | 2/1998 |
| JP | 07002628 | * | 10/1987 |
| JP | 01132510 | * | 5/1989 |
| WO | 88/01502 A | | 3/1988 |

OTHER PUBLICATIONS

Rolland, A., et al., "Site Specific Drug Delivery to Pilosebaceous Structures Using Polymeric Microspheres", Pharmaceutical Research, vol. 10, No. 12, 1993, New York, NY, (pp. 1738-1744).
European Search Report issued Aug. 5, 2009, in counterpart EPO Application No. 07122233.5-2404/1901064.

* cited by examiner

*Primary Examiner*—D L Jones
(74) *Attorney, Agent, or Firm*—Townsend & Banta

(57) ABSTRACT

A method for measuring skin absorbability of a substance, which includes measuring the amount of the substance which is penetrated into hair follicles; and using the resultant data as an index representing the amount of the substance which is absorbed through skin pores, to thereby determine the amount of the substance absorbed through skin pores and a method for measuring skin absorbability of a substance, which includes bringing the substance into contact with a first surface of a thin film that mimics the skin surface layer, a second surface of the film being brought into contact with artificial sebum; and evaluating the sebum transferability of the substance by using the degree of transfer of the substance to the artificial sebum as an index, are disclosed. A kit for performing the measurement method of the present invention is also disclosed.

1 Claim, 20 Drawing Sheets

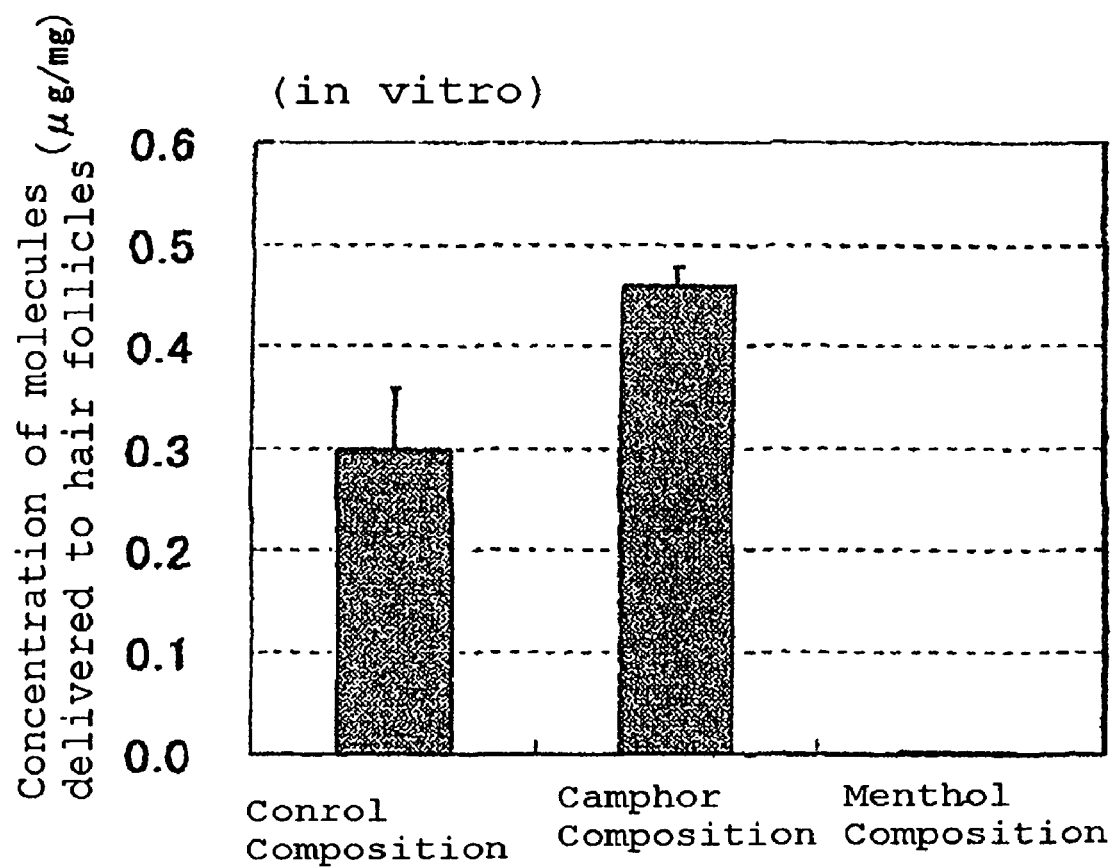

METHOD FOR MEASURING SKIN ABSORBABILITY

CROSS REFERENCE TO A RELATED APPLICATIONS

This is a divisional patent application of application Ser. No. 10/238,520, filed Sep. 9, 2002, now abandoned, which was a divisional application of U.S. patent application Ser. No. 09/697,043, filed Oct. 27, 2000, now abandoned.

BACKGROUND OF THE INVENTION

1. Field of the Invention

The present invention relates to a method for screening an ingredient which is to be applied to the hair; a kit for carrying out the screening; and a composition comprising an ingredient exhibiting effects to accelerate absorption of an active ingredient through skin pores (hereinafter the absorption will be referred to as "skin-pore absorption") and transfer of the active ingredient to sebum, the effects being confirmed by means of the screening method.

2. Background Art

An important step in the development of a hair-growing agent is to confirm that an active ingredient exhibits excellent hair-growing effect and has penetrability so as to reliably reach a target site. Whether or not the active ingredient reliably reaches the target site greatly depends on the properties of the active ingredient or the base ingredient of the hair-growing agent.

The mechanism of absorption of a drug or an active agent through hair follicles has become of interest, since hair follicles are considered to be an effective route through which a hair-growing agent as well as a vaccine or a gene can be administered.

The degree of transfer of a drug to sebum (hereinafter the degree will be referred to as "sebum transferability") has been reported to influence whether the drug easily reaches a target site in the skin (e.g., hair follicles or sebaceous gland) (Critical Reviews, 14 (3): 207 219 (1997)).

The penetrability of a drug through the hair follicles has been studied, for example, by the following methods:

(1) a method for observing tissue sections by means of fluorescence labeling or radioisotopes (Suzuki, M., et al., J. Soc. Cosmet. Chem. (1978), Nicholau, G., et al., Xenobiolica (1987), Lieb, L. M., et al., J. Invest. Dermatol. (1995)) and (2) a method for comparing hairy skin and hairless skin with respect to the transdermal permeability of a drug (e.g., comparison of hairless rat and hairy rat: Illel, B., et al., J. Pherm. Sci. (1991); comparison of normal human skin and skin which has received burns and has subsequently healed: Hueber, F., et al., J. skin Pharmacologic. (1994)).

However, method (1) is qualitative rather than quantitative, and the method involves the time-consuming preparation of tissue sections. In method (2), absorption of a drug is studied only from the viewpoint of transdermal absorption, and "skin-pore absorption" and "sebum transferability," which are important properties of a hair-growing agent, cannot be confirmed directly.

Therefore, the aforementioned conventional methods encounter difficulty in directly confirming that a drug reaches a target site in the skin and exerts the intended effects.

SUMMARY OF THE INVENTION

In view of the foregoing, an object of the present invention is to provide means for conveniently and reliably determining the degree of skin-pore absorption (hereinafter the degree will be referred to as "skin-pore absorbability") and sebum transferability of a substance such as a drug, the skin-pore absorbability and sebum transferability being indexes for directly confirming that the substance reaches a target site in the skin and exerts the desired effects. Another object of the present invention is to provide a composition for the scalp and hair which exhibits excellent skin-pore absorbability and sebum transferability and which enables a drug contained in the composition to reliably reach a target site in the skin, the skin-pore absorbability and the sebum transferability being determined through the means of the present invention.

The sebum transferability of a drug is considered a useful index to evaluate whether or not the drug easily reaches a specific target site in the skin, but can not be easily evaluated in vivo. Therefore, a specific object of the present invention is to provide means for accurately and conveniently evaluating the sebum transferability of a drug in vitro.

The present inventors have performed extensive studies, and have found that, when the amount of a substance which is penetrated into hair follicles, the amount being determined in vitro or in vivo, is employed as an index of the amount of the substance which is absorbed through skin pores, the skin-pore absorbability of the substance can be conveniently and reliably determined, to thereby measure the skin absorbability of the substance.

As used herein, the term "skin-pore absorption" refers to absorption through skin pores, although the term "transdermal absorption" refers to absorption through any portion of the skin (i.e., over the entire skin area). Therefore, as described below, a drug which exhibits transdermal absorbability does not necessarily exhibit skin-pore absorbability. In addition, because a hair-growing agent exerts its actions in the vicinity of the hair follicle, evaluating the "skin-pore absorbability" of the agent is very important.

The present invention provides a method for the measurement of skin absorbability of a substance (hereinafter the method will be referred to as "measurement method 1"), which comprises measuring the amount of a substance which is penetrated into the hair follicles; and using the resultant data as an index representing the amount of the substance which is absorbed through the skin pores, to thereby determine the skin-pore absorbability of the substance.

If the phenomenon of "skin-pore absorption" is considered from the function of absorption, penetration of a substance into hair follicles substantially occurs through skin pores. Therefore, in the present invention, "absorption through skin pores" or "skin-pore absorption" and "absorption through hair follicles" or "transfollicular absorption" are used as terms having the substantially same meaning.

Accordingly, measurement method 1 is also provided as a method for the measurement of skin absorbability of a substance, which comprises measuring the amount of a substance which is penetrated into the hair follicles; and using the resultant data as an index representing the amount of the substance which is absorbed through the hair follicles, to thereby determine the transfollicular absorbability of the substance.

Measurement method 1 is classified into the following two methods:

(1) an in vitro quantification method (hereinafter referred to as "measurement method 1-1") in which the amount of a substance (e.g., a drug) which is penetrated into the hair follicle or skin tissue is determined by applying the substance to a model skin having a pseudo-biological state, removing the hair follicle from the dermis or skin tissue of the skin model, and measuring the concentration of substance which is delivered to the hair follicle or skin tissue; and (2) an in vivo quantification method (hereinafter referred to as "measurement method 1-2") in which the amount of a substance (e.g., a drug) which is penetrated into the hair follicle is determined by applying the substance to the human scalp, removing the hair follicle from the scalp, and measuring the concentration of the substance which is delivered to the hair follicle.

The present inventors have also found that the sebum transferability of a substance can be easily evaluated in vitro by use of a skin model comprising artificial sebum.

The present invention also provides a method for the measurement of skin absorbability of a substance (hereinafter the method will be referred to as "measurement method 2"), which comprises bringing a substance into contact with a first surface of a film that mimics the skin surface layer, a second surface of the film being brought into contact with artificial sebum; and using the degree of transfer of the substance to the artificial sebum as an index, to thereby evaluate the sebum transferability of the substance.

The present inventors have also found that, by means of measurement methods 1 and 2, an oily ingredient having an I.O.B. value of 0.06-4.0 exhibits excellent effects of accelerating skin-pore absorption and sebum transfer of extensive polar substances from water-soluble substances to fat-soluble substances.

The present invention also provides a composition for the scalp and hair comprising an oily ingredient having an I.O.B. value of 0.06-4.0 (hereinafter the composition may be referred to as "the composition of the present invention").

As used herein, I.O.B. (Inorganic/Organic Balance) value refers to an index representing the polarity of an oily ingredient (hereinafter the term "oily ingredient" includes fats and oils, waxes, hydrocarbon oils, higher fatty acids, higher alcohols, esters, general alcohols, and fatty acids). The I.O.B. value represents the ratio of an inorganic value of the oily ingredient to an organic value of the oily ingredient (note: the ratio is calculated as follows: an organic value of 20 is assigned for each carbon atom in the molecule of the oily ingredient, and an inorganic value of 100 is assigned per hydroxyl group in the molecule of the oily ingredient, and these values are used as yardsticks for calculating an inorganic value for another substituent (inorganic group); see (1)"Organic Analysis" authored by Fujita (1930), published by Kaniya Shoten, (2) "Prediction of Organic Compounds and Organic Conceptual Diagram ("Kagaku-no-Ryoiki 11-10" (1957), pp. 719-725, authored by Fujita, (3) "Systematic Organic Qualitative Analysis (Book of Purified Substances)" (1970), p 487, authored by Fujita and Akatsuka, published by Kazama Shoten, (4) "Organic Conceptual Diagram, Its Fundamentals and Applications" (1984), p 227, authored by Koda, published by Sankyo Shuppan, (5) "Design of Emulsion Formulations by use of Organic Conceptual Diagram" (1985), p 98, authored by Yaguchi, published by Nippon Emulsion K. K., and (6) R. H. Ewell, J. M. Harrison, L. Berg.: Ind. Eng. Chem. 36, 871 (1944)), and is expressed by:

I.O.B.=inorganic value of the oily ingredient/organic value of the oily ingredient.

A typical product form of the composition of the present invention; i.e., the composition which is to be applied to the scalp and hair, is a hair-growing agent, but the composition is not particularly limited to the product form. For example, the composition may assume a variety of product forms, including compositions for treating hair, such as a hair-removing agent, a hair-dyeing agent, and a hair-bleaching agent; compositions for washing hair, such as shampoo and rinse-in-shampoo; compositions for protecting hair, such as a rinse and a treatment agent; gray-hair prevention agents; cosmetics which are absorbed through the skin excluding the scalp; and drugs such as vaccines and genetic drugs.

According to the present invention, there is provided means for conveniently and accurately measuring the skin absorbability of a test substance through quantification of the skin-pore absorbability or sebum transferability of the test substance. By means of the method, there is provided means for accelerating the skin-pore absorption or sebum transfer of a drug or an active ingredient, for example in a hair-growing agent, by which the drug or active ingredient effectively reach the target site; i.e., the hair follicle.

BRIEF DESCRIPTION OF THE DRAWINGS

The foregoing and other objects, features, and many of the attendant advantages of the present invention will be readily appreciated as the same becomes better understood with reference to the following detailed description of the preferred embodiments when considered in connection with accompanying drawings, in which:

FIG. 11A and FIG. 11B show the results of the evaluation of refreshing agents by means of measurement method 1-1.

DETAILED DESCRIPTION OF PREFERRED EMBODIMENTS

Figure 1A:
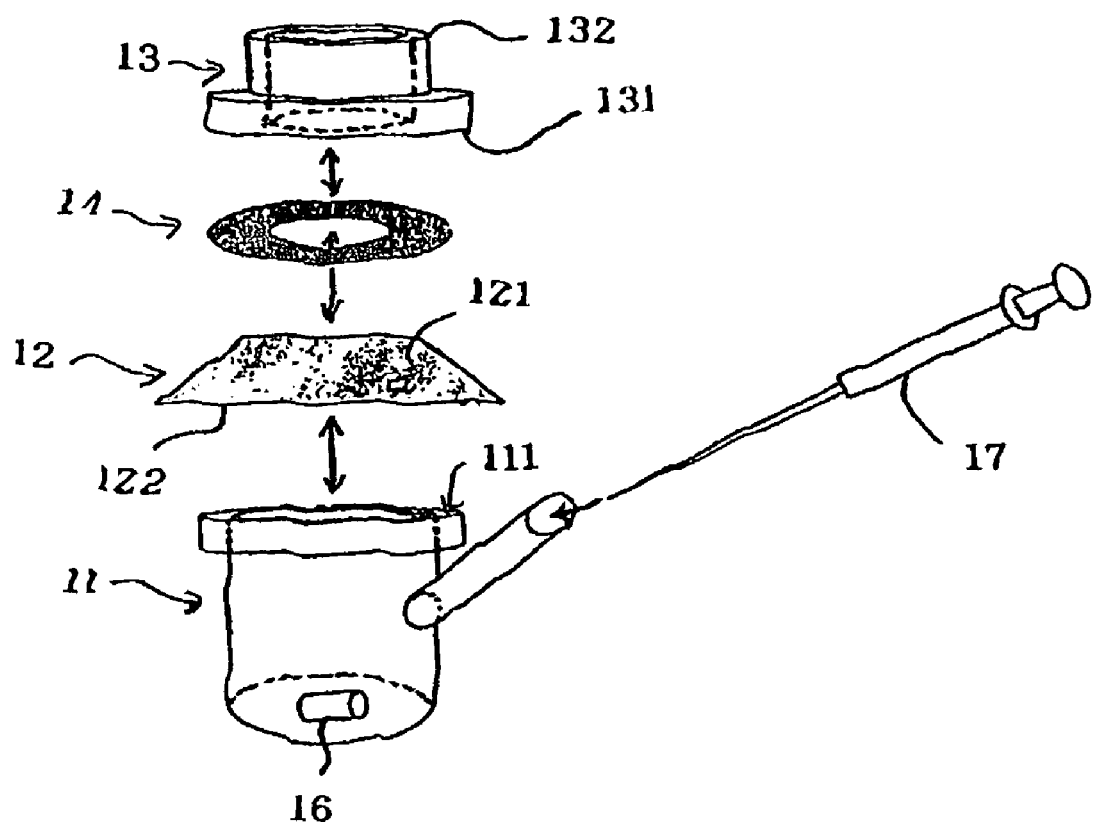
FIG. 1A and FIG. 1B are schematic representations showing an embodiment of the kit of the present invention.

Embodiments of the present invention will next be described.

A. Measurement Method 1

Measurement Method 1-1

Measurement method 1-1 is an embodiment of measurement method 1 carried out in vitro.

In measurement method 1-1, the skin of a model animal or the skin reconstructed from skin cells may be employed as a skin model. The model animal from which the skin is taken is not particularly limited, and pig, human, cattle, mouse, or rat are all potential donors. In measurement method 1-1, the skin of a hairy animal is usually employed in order to evaluate the penetrability of a drug through skin pores into hair follicles. Therefore, a mutated hairless animal is usually unsuitable for the model animal. In addition, in view that measurement method 1-1 is employed for the screening of a drug which is to be ultimately applied to humans, the skin of a model animal which is employed in the method preferably mimics that of a human. Therefore, other than human, pig is preferably employed as a model animal.

In measurement method 1-1, the phrase "the skin has a pseudo-biological state" refers to the case in which the skin specimen is highly analogous to the skin of a living organism. The skin is not particularly limited, so long as the skin satisfies the above condition. For example, as described below in the Example, a skin model may be fixed onto a collagen gel.

Thus, a substance such as a drug is applied to a skin model specimen having a pseudo-biological state, the hair follicles are removed from the dermis of the skin model specimen, and the amount of the substance which is delivered to the hair follicle is quantified. The delivery amount may be employed as an index of the skin-pore absorbability of the substance.

The conditions for the application of the substance may be arbitrarily determined in accordance with the type of the substance or the object. Usually, the skin to which the substance is applied is incubated at about 37° C. (near the temperature of the human body) over a predetermined time period. The incubation time varies with the intended product form of the substance.

The portion at which the delivery amount of the substance is measured is limited to the region corresponding to the dermis of the skin, since in the region corresponding to the stratum corneum or epidermis of the skin, the hair follicle may be contaminated with epidermal tissue debris or excretions from the sebaceous glands, and thus the exact delivery amount of the substance is difficult to measure.

The method for measuring the delivery amount of the substance is not particularly limited. For example, liquid chromatography (including high-performance liquid chromatography), a fluorescent antibody technique using a fluorescence-labeled antibody, mass spectrometry, or a method using a radioisotope may be employed. Of these, liquid chromatography is preferable, in consideration of convenience.

When the amount of the substance which is delivered to the hair follicle is large, the amount being measured through the aforementioned method, the substance is considered to have excellent skin-pore absorbability. Incidentally, conventional qualitative measurement methods provide limited information about the substance; i.e., whether or not the substance has skin-pore absorbability.

The skin absorbability of a substance such as a drug can be also quantified as follows: the amount of the substance penetrated into hair follicles and the amount of the substance penetrated into different portions of the skin tissue, such as the stratum corneum, epidermis or dermis are determined and the resultant data is used as an index of the amount of the substance which is absorbed through hair follicles and percutaneously.

Thus, the skin absorbability of a substance is measured by means of measurement method 1-1.

Measurement Method 1-2

In measurement method 1-2, a method for the application of a substance such as a drug to the human scalp may be arbitrarily determined in accordance with the characteristics or the intended product form of the substance.

After the substance is applied to a person participating in the test, several hair strands from the person are removed, and the thus-obtained hair follicles may be stored as hair shafts and/or outer root sheaths. The amount of the substance which is delivered to the subcutaneous portion of the hair shaft and/or the outer root sheath is measured, and the thus-obtained delivery amount of the substance may be employed as an index of the skin-pore absorbability of the substance.

The delivery amount of the substance may be measured in a manner similar to that of measurement method 1-1.

Thus, the skin absorbability of the substance is measured through measurement method 1-2.

In measurement method 1-2, evaluation of a substance requires removal of human hair. Therefore, when a variety of substances are to be evaluated for skin-pore absorbability, measurement method 1-2 is not necessarily appropriate. In order to evaluate the skin-pore absorbability of the substances, it is preferable that firstly, they are screened through measurement method 1-1, and of the resultant screened substances, those which exhibit relatively high skin-pore absorbability are further evaluated through measurement method 1-2.

B. Measurement Method 2

Artificial sebum which is employed in measurement method 2 is a mixture of oils and fats, and the mixture can be prepared on the basis of the composition of natural sebum.

Examples of oily ingredients which are incorporated in the artificial sebum include, but are not limited to, triglyceride, C14-C18 saturated fatty acids, C14-C18 unsaturated fatty acids, squalene, squalane, cholesterol, and C18-C72 wax esters.

A specific example formulation of the artificial sebum will be described in the Example.

In order to accurately evaluate the transferability of a substance, the artificial sebum preferably assumes a fluid state. The fluid state is easily formed by stirring of the artificial sebum by use of, for example, a magnetic stirrer.

When a surface of a thin film which mimics the real skin not containing the dermis (hereinafter the film may be simply referred to "thin film") is brought into contact with the artificial sebum, a structure similar to that of the skin surface may be approximated. In this case, a structure similar to that of the surface layer of the skin is reproduced, since the aperture of the sebaceous gland (a sebum supply source) is present in the surface layer. Therefore, a surface of the thin film to which a substance such as a drug is applied is preferably analogous to the surface layer of the skin, in order to reproduce the state in which the substance is applied to the skin. Specifically, a substrate film may be formed of a thin film which exhibits no surface reactivity, such as a single-layer silicone film, a polyethylene carbonate film, a cellulose film, or another polymer film. A surface of the substrate film is subjected to keratinization or powder treatment, in order to form a structure similar to that of the stratum corneum. The resultant treated side of the thin film is regarded as the stratum corneum (hereinafter the side may be referred to as "stratum corneum side), to which a substance is applied in the present invention.

The sebum transferability of a substance may be evaluated through the following procedure: the substance is applied to the stratum corneum side of the thin film, the opposite side of the stratum corneum side being brought into contact with the artificial sebum; the degree of transfer of the substance to the artificial sebum, for example, the amount of the substance transferred to the sebum per unit time, i.e., the amount of the substance contained in the sebum is measured; and the amount of the substance in the sebum is employed as an index, to thereby evaluate the sebum transferability of the substance.

The method for measuring the amount of the substance contained in the artificial sebum is not particularly limited, and a customary method may be arbitrarily employed in accordance with the characteristics of the substance. For example, high-performance liquid chromatography, thin-layer chromatography, or mass spectrometry may be employed.

In measurement method 2, in order to reproduce the case in which a drug is actually applied to the skin, the stratum corneum side of the thin film is preferably made open to the air. However, the stratum corneum side may be closed in accordance with the intended use of a drug (for example, when the penetration acceleration effect of the drug is intended to be effected in a closed state).

Measurement method 2 is specifically carried out through the following preferred embodiment.

The present invention provides a kit for carrying out measurement method 2 (hereinafter the kit may be referred to as "the kit of the present invention") comprising:

(1) a sealable receptacle in which artificial sebum is placed, the receptacle comprising an opening which includes a fixing means enabling fixation of a thin film so as to cover the opening in the state in which the thin film is removable;

(2) a thin film which mimics the skin surface layer, which film is to be applied and fixed onto the opening of the sealable receptacle so as to cover the opening; and (3) artificial sebum which is to be placed in the sealable receptacle.

Figure 1B:
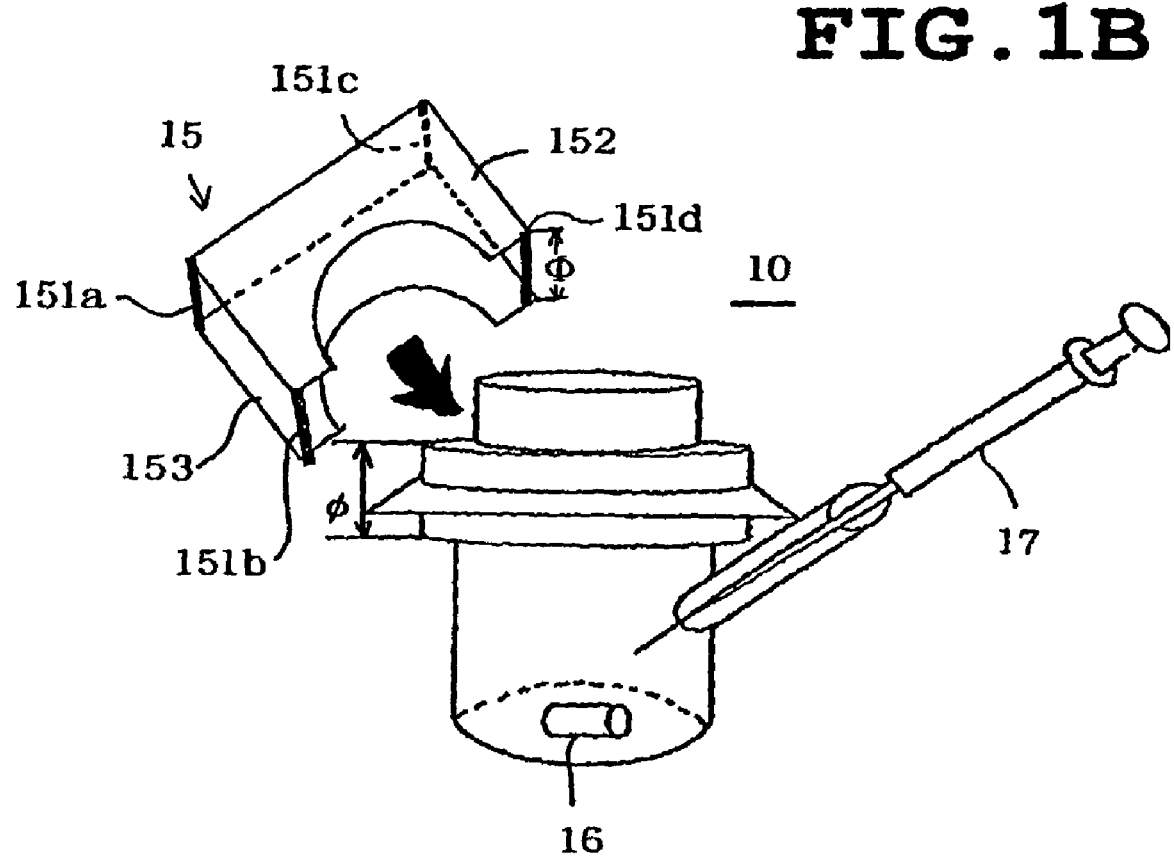

The kit of the present invention will be described with reference to FIGS. 1A and 1B. FIGS. 1A and 1B are schematic representations showing an embodiment of the kit of the present invention.

With reference to FIG. 1A, a sealable receptacle 11 is a cylindrical container, one side of the container being an opening 111 and the other serving as the bottom. A protuberant portion of the opening 111 protrudes towards the outside and around the circumference of the receptacle 11.

The sealable receptacle 11 is preferably formed from a transparent material in order to permit easy observation of the inside of the receptacle. To enable easy removal of the artificial sebum from the sealable receptacle, the receptacle is preferably formed from a material which does not cause leakage of the contents even when a needle such as an injection needle is inserted through the receptacle wall.

The thin film 12 exhibits no surface reactivity, and a first surface 121 of the film is subjected to keratinization so as to form a state analogous to the skin surface layer.

When the kit is used, the thin film 12 is fixed onto the opening 111 of the receptacle 11 so as to cover the opening (usually, the first surface 121 of the film is directed towards the outside of the receptacle 11, and a second surface 122 of the film is directed towards the inside of the receptacle 11). The sealable receptacle 11 must be provided with the entirety or a part of a fixing means which enables fixing of the thin film on the opening, so that the thin film can be fixed on or removed from the opening. In the present embodiment, a thin-film fixing member 13 is employed as the primary fixing means.

The thin-film fixing member 13 has two openings (openings 131 and 132) formed at opposite ends. The protuberant portion of the opening 131 protrudes towards the outside and around the circumference of the member, and the protuberant portion can be engaged with the corresponding protuberant portion of the opening 111 of the receptacle 11. The structure of these protuberant portions is not particularly limited, so long as they can engage with each other. For example, these portions may have a concave-convex structure so as to enable coupling of the portions. In addition, arbitrary means may be employed in order to enhance the degree of engagement or sealing between the sealable receptacle 11 and the member 13.

As shown in FIG. 1A, a packing 14 is provided between the first surface 121 of the thin film 12 and the thin-film fixing member 13, to thereby form the conjunction structure "thin-film fixing member 13—packing 14—thin film 12—sealable receptacle 11". As a result, the degree of engagement or sealing between the sealable receptacle 11 and the member 13 can be enhanced. In general, the packing 14 may be formed from rubber such as silicone rubber, synthetic rubber, or natural rubber. Of these, silicone rubber is preferable, in consideration of corrosion resistance.

In the kit of the present invention, in order to fix the conjunction structure "thin-film fixing member 13—packing 14—thin film 12—sealable receptacle 11", a fixing member 15 as shown in FIG. 1B may be employed. The fixing member 15 comprises two plate members (152 and 153) and four supporting bars (151a, 151b, 151c, 151d), the length ($\Phi$) of the bars being slightly longer than the length ($\phi$) of the conjunction portion of the conjunction structure "thin-film fixing member 13—packing 14—thin film 12—sealable receptacle 11". The plate members are maintained to be parallel to each other through support of the bars. The fixing member 15 may comprise a structure which enables adjustment of the length ($\Phi$) of the bars. For example, a screw structure which enables adjustment of the length ($\Phi$) may be provided with the supporting bars (151a, 151b, 151c, and 151d), to thereby adjust the length ($\Phi$) in accordance with the length ($\phi$). The plate members 152 and 153 have a concave portion so that the fixing member 15 can be fitted to the openings 111 and 113. The size of the concave portion is larger than that of the circumferential portion of the openings 111 and 131.

When the conjunction portion of the conjunction structure "thin-film fixing member 13—packing 14—thin film 12—sealable receptacle 11" is fitted with the concave portion of the fixing member 15 and then the conjunction portion is placed within the space of the fixing member 15, the space being defined by the supporting bars, the conjunction portion can be supported by the supporting force of the bars (151a, 151b, 151c, and 151d) between the plate members 152 and 153. The conjunction portion may be fixed by use of a clip instead of the fixing member 15 having the aforementioned structure.

FIG. 1B shows an embodiment of use of the kit 10. The thin film 12 is sandwiched, via the packing 14, by the sealable receptacle 11 and the thin-film fixing member 13, to thereby form the conjunction structure "thin-film fixing member 13—packing 14—thin film 12—sealable receptacle 11". The thin film 12 is fixed onto the opening 111 of the sealable receptacle 11 in which the artificial sebum is placed, so as to cover the opening. The surface 121 which has undergone keratinization is directed to the upper side, and the surface 122 is brought into contact with the artificial sebum in the sealable receptacle 11. A magnetic stirrer 16 is placed on the bottom of the sealable receptacle 11, and thus the artificial sebum can assume a fluid state. The conjunction portion may be fixed by means of the fixing member 15.

A substance is brought into contact with the surface 121 of the thin film 12 through the opening 132 of the thin-film fixing member 13. The sebum transferability of the substance is evaluated by determining the degree of transfer of the substance, via the thin film 12, to the artificial sebum in the sealable receptacle 11. When evaluating the sebum transferability of the substance is to be carried out in a closed system, the opening 132 may be closed by use of a cap.

The degree of transfer of the substance to the artificial sebum can be determined by analysis of the sebum after sampling by use of a syringe 17.

Thus, the skin absorbability of the substance can be measured by means of measurement method 2.

B. Composition of the Present Invention

As described below in the Example, an oily ingredient having an I.O.B. value of 0.06-4.0 exhibits effects which accelerate the skin-pore absorption or sebum transfer of a drug, the effects being confirmed by means of measurement method 1 or 2.

Briefly, when one or more oily ingredients having an I.O.B. value of 0.06-4.0 are incorporated into a composition for the scalp and hair which may assume the product form of a hair-growing agent, penetration of a hair-growing ingredient through skin pores into hair follicles can be accelerated, the hair follicles being the target of the agent. When the oily ingredient has an I.O.B. of less than 0.06 or in excess of 4.0, the oily ingredient tends not to exhibit the desired effects of accelerating the skin-pore absorption or sebum transfer of the agent.

Specifically, an oily ingredient having an I.O.B. value of 0.06-4.0 preferably has an organic value of 100-750 and an inorganic value of 50-400. More preferably, the oily ingredient has an inorganic value of 100-400.

Preferably, an oily ingredient having an I.O.B. value of 0.06-4.0 is a hydrocarbon derivative which is liquid at ambient temperature and has a backbone structure of a C6-C18 hydrocarbon. The hydrocarbon derivative is preferably an amphipathic substance which is liquid at ambient temperature. When the hydrocarbon derivative is liquid at ambient temperature, the number of carbon atoms of the derivative is usually 24 or less. Examples of the hydrocarbon derivative include, but are not limited to, fatty acids, alcohols, amides, and esters. Of these, alcohols or fatty acids are preferable.

Specific examples of the aforementioned oily ingredient include lauryl alcohol (I.O.B. value 0.41: organic value 240, inorganic value 100), lauric acid (I.O.B. value 0.68: organic value 220, inorganic value 150), lauric acid ethanolamide (I.O.B. value 1.25: organic value 240, inorganic value 300), lauric acid diethanolamide (I.O.B. value 1.53: organic value 260, inorganic value 400), monoglyceryl laurate (I.O.B. value 0.92: organic value 280, inorganic value 260), diglyceryl laurate (I.O.B. value 0.32: organic value 500, inorganic value 160), oleyl alcohol (I.O.B. value 0.28: organic value 360, inorganic value 102), oleic acid (I.O.B. value 0.45: organic value 340, inorganic value 152), oleic acid ethanolamide (I.O.B. value 0.83: organic value 360, inorganic value 302), oleic acid diethanolamide (I.O.B. value 1.05: organic value 380, inorganic value 402), monoglyceryl oleate (I.O.B. value 0.66: organic value 400, inorganic value 262), diglyceryl oleate (I.O.B. value 0.30: organic value 740, inorganic value 222), isostearyl alcohol (I.O.B. value 0.29: organic value 350, inorganic value 100), isostearic acid (I.O.B. value 0.45: organic value 330, inorganic value 150), isostearic acid ethanolamide (I.O.B. value 0.86: organic value 350, inorganic value 300), isostearic acid diethanolamide (I.O.B. value 1.08: organic value 370, inorganic value 400), monoglyceryl isostearate (I.O.B. value 0.66: organic value 390, inorganic value 260), diglyceryl isostearate (I.O.B. value 0.30: organic value 730, inorganic value 220), stearyl alcohol (I.O.B. value 0.27: organic value 360, inorganic value 100), stearic acid (I.O.B. value 0.44: organic value 340, inorganic value 150), stearic acid ethanolamide (I.O.B. value 0.83: organic value 360, inorganic value 300), stearic acid diethanolamide (I.O.B. value 1.05: organic value 380, inorganic value 400), monoglyceryl stearate (I.O.B. value 0.67: organic value 390, inorganic value 260), diglyceryl stearate (I.O.B. value 0.30: organic value 740, inorganic value 220), and benzyl alcohol (I.O.B. value 0.96: organic value 120, inorganic value 115). Of these, lauryl alcohol, lauric acid, isostearic acid, isostearyl alcohol, monoglyceryl isostearate, or isostearic acid ethanolamide are preferable, and isostearyl alcohol is more preferable.

Terpenes do not necessarily satisfy the above condition; i.e., I.O.B. value of 0.06-4.0, but they tend to exhibit excellent effects to accelerate the skin-pore absorption of a drug or an active ingredient. Particularly, camphor, among terpenes, exhibits the excellent effect of accelerating skin-pore absorption.

The composition of the present invention comprises an oily ingredient having an I.O.B. value of 0.06-4.0, such as isostearyl alcohol, as an ingredient which accelerates skin-pore absorption of an active ingredient of a drug or transfer of the active ingredient to sebum (the composition may comprise a terpene such as camphor serving as an ingredient which accelerates skin-pore absorption of the active ingredient, singly or in combination with the oily ingredient having an I.O.B. value of 0.06-4.0). The oily ingredient or a terpene may be incorporated into the composition so as to attain another object. For example, isostearyl alcohol may serve as an oily agent, a solvent for a drug, or a sebum-dissolving agent. A terpene such as camphor may serve as a refreshing agent or a blood-circulation-stimulating agent.

The amount of the oily ingredient having an I.O.B. value of 0.06-4.0 in the composition of the present invention is not particularly limited, since the amount of the ingredient varies in accordance with the product form or use of the composition.

When the composition assumes the product form of a hair-growing agent and when the oily ingredient is intended to exhibit effects for accelerating the skin-pore absorption or sebum transfer of an active ingredient of the agent, the oily ingredient is incorporated into the composition in an amount of 1 ppm-20% by weight of the composition, preferably 0.01-5% by weight of the composition.

The composition of the present invention may contain, in addition to the oily ingredient having an I.O.B. value of 0.06-4.0, pharmaceutically active ingredients or base ingredients in accordance with a specific product form of the composition.

For example, when the composition assumes the product form of a hair-growing agent, the composition may contain the following pharmaceutically active ingredients: blood-circulation-stimulating agents such as Swertia herb extract, cepharanthine, vitamin E and it derivatives, γ-oryzanol, and raspberry extract; topical stimulation agents such as capsicum tincture, ginger tincture, cantharides tincture, and benzyl nicotinate; nutrition agents such as vitamins and amino acids; female hormones such as estradiol and ethinylestradiol; hair-root activators such as pantothenic acid and its derivatives, placental extract, allantoin, and photosensitive pigment 301; and anti-inflammatory agents such as glycyrrhetic acid and glycyrrhizinic acid.

The oily ingredient having an I.O.B. value of 0.06-4.0 which is incorporated into the composition as an essential ingredient accelerates the skin-pore absorption or sebum transfer of the pharmaceutically active ingredient, and enhances the penetrability of the active ingredient into the hair follicle.

The composition of the present invention may further contain any known ingredient. Examples of known ingredients include humectants, corneocyte desquamating agents, refreshing agents, oily ingredients, surfactants, silicones, ultraviolet absorbents, perfumes, and water.

EXAMPLES

The present invention will next be described in more detail by way of Examples, which should not be construed as limiting the invention thereto. Unless otherwise specified, the incorporation amount of an ingredient is represented by wt. % of the composition.

Measurement Method 1-1

1. Evaluation of Accuracy of Measurement Method 1-1

In the evaluation test, 0.5% pantothenyl ethylether (90% ethanol product) was employed as a substance to be tested, and the skin of a miniature pig (Yucatan Micropig Skin Set: product of Charles River) was employed as a skin model.

Figure 2:
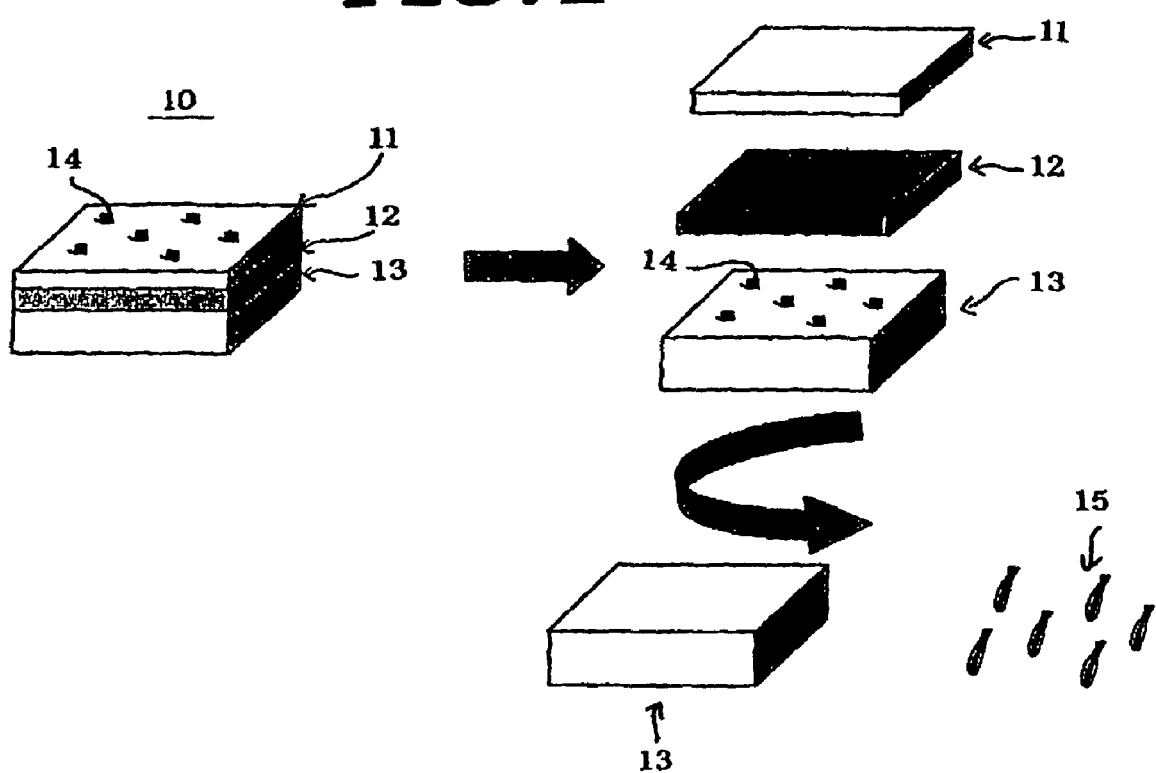
FIG. 2 is a schematic representation to elucidate measurement method 1-1.

As shown in FIG. 2, a skin sample 10 from the miniature pig (size: 2 cm×2 cm) (the sample including a stratum corneum 11, epidermis 12, and dermis 13) was prepared, and the sample was fixed onto a collagen gel, to thereby assume a pseudo-biological state. The test sample (20 μl) was applied onto the skin sample comprising skin pores 14. The substance was applied onto a region (diameter: 1.5 cm) of the sample; i.e., within an assay ring to which silicon grease was applied. The resultant skin sample 10 was allowed to stand at 37° C. for 16 hours. After having being washed, the sample 10 was separated into the stratum corneum 11, the epidermis 12, and the dermis 13. Subsequently, hair follicles 15 were removed from the dermis 13, and the amount of pantothenyl ethylether contained in the follicles was measured, as a delivery amount per unit weight of the hair follicle, by means of liquid chromatography (NANOSPACE (product of Shiseido Co., Ltd.), eluent: ($CH_3CN:H_2O$=3:7), detection wavelength: 210 nm).

The skin sample 10 of the miniature pig was derived from the upper back and lower back (n=3).

Figure 3:
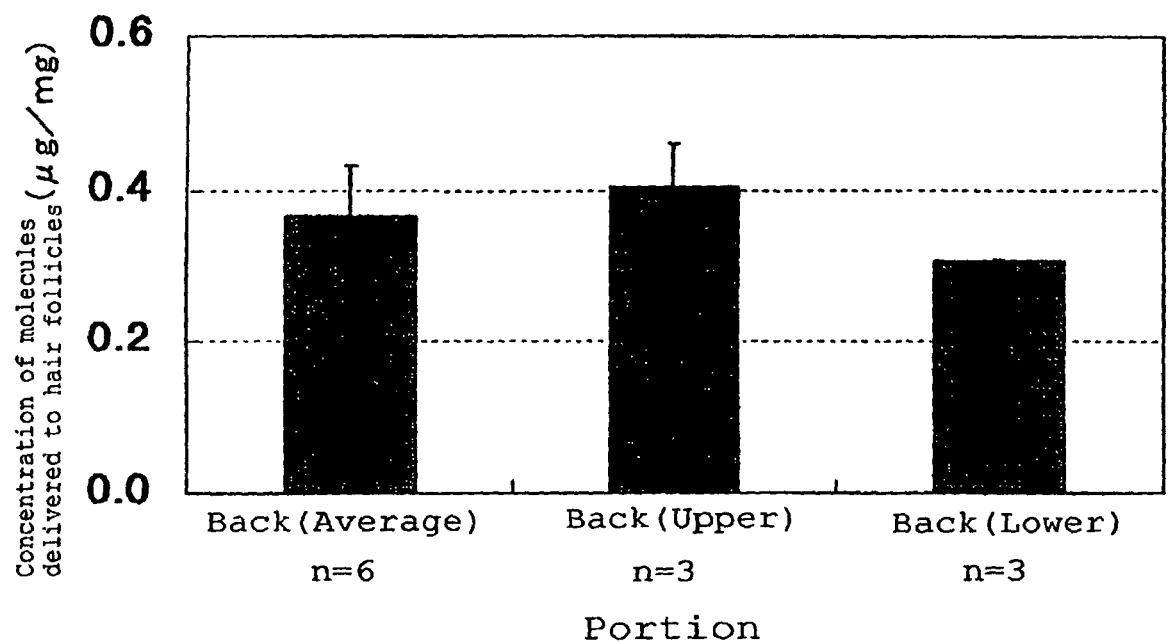
FIG. 3 shows the results of the evaluation test of the accuracy of measurement method 1-1.

The results of the test are shown in FIG. 3. In FIG. 3, the vertical axis corresponds to the concentration of pantothenyl ethylether delivered to the follicles per unit weight of the hair follicle. As is apparent from FIG. 3, the portion from which the samples were prepared exhibits little influence on data. The results show that data of high reproducibility can be obtained by means of measurement method 1-1.

2. Evaluation of Ingredient by Means of Measurement Method 1-1

(1) Ingredient Evaluation Test 1

Test samples; i.e., a control composition (ethanol product) and a 5% isostearyl alcohol-containing composition, were prepared. Formulations of the respective compositions are shown in Table 1.

TABLE 1

| Ingredient (wt. %) | Control composition | 5% Isostearyl alcohol composition |
| --- | --- | --- |
| Ethanol | 89.5 | 84.2 |
| Polyoxyethylene hydrogenated castor oil (40 E.O.) | — | 0.1 |
| Isostearyl alcohol | — | 5.0 |
| Isostearic acid | — | 0.2 |
| Ion-exchange water | 10.0 | 10.0 |
| Pantothenyl ethylether | 0.5 | 0.5 |

Figure 4:
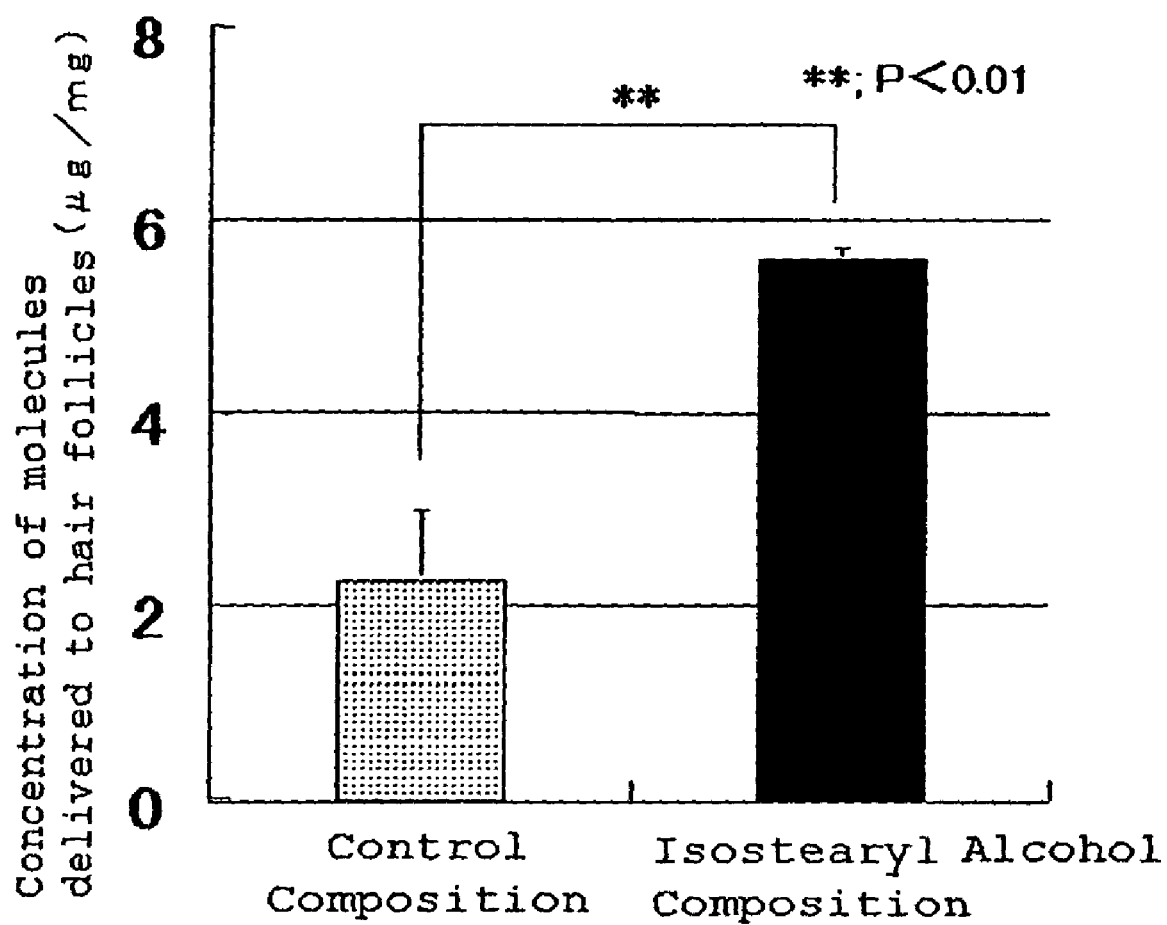
FIG. 4 shows the results of the ingredient evaluation by means of measurement method 1-1.

The amount of each of the test samples (the control composition and the 5% isostearyl alcohol-containing composition) which was absorbed through skin pores was measured in a manner similar to that of the above accuracy test. Skin samples were derived from the upper back and lower back of the miniature pig (n=5). The results of the evaluation test are shown in FIG. 4. As is apparent from FIG. 4, the concentration of pantothenyl ethylether delivered to hair follicles increases significantly in the presence of isostearyl alcohol.

In the test, the concentration of pantothenyl ethylether delivered to the stratum corneum, the epidermis, and the dermis of each skin sample was measured by means of liquid chromatography as described above. The results are shown in FIG. 5A, FIG. 5B, and FIG. 5C.

Figure 5A:
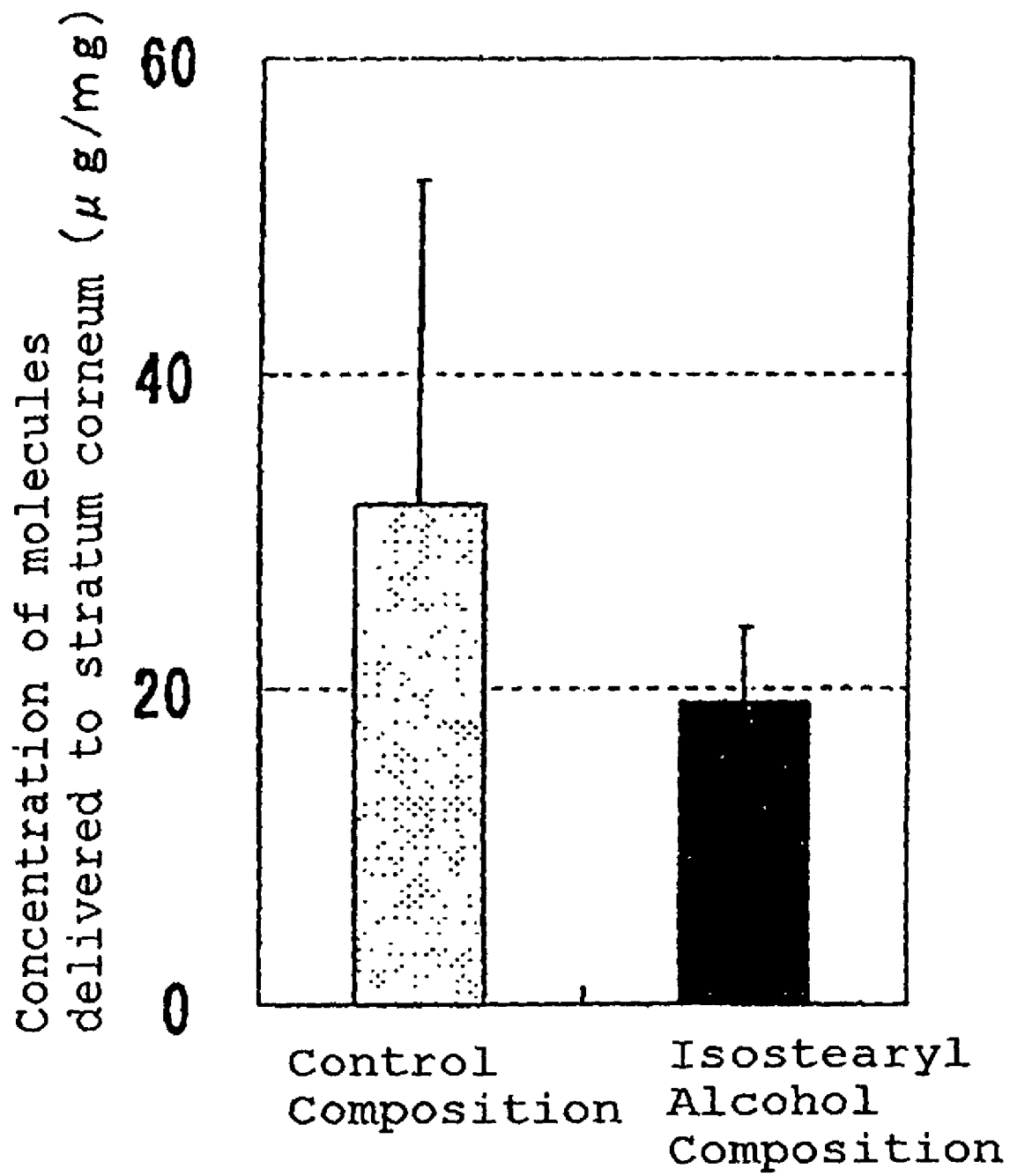
FIGS. 5A to 5C show the results of a test in which the concentrations of pantothenyl ethylether delivered to the stratum corneum (FIG. 5A), the epidermis (FIG. 5B), and the dermis (FIG. 5C) of a skin sample are measured by means of measurement method 1-1.
Figure 5B:
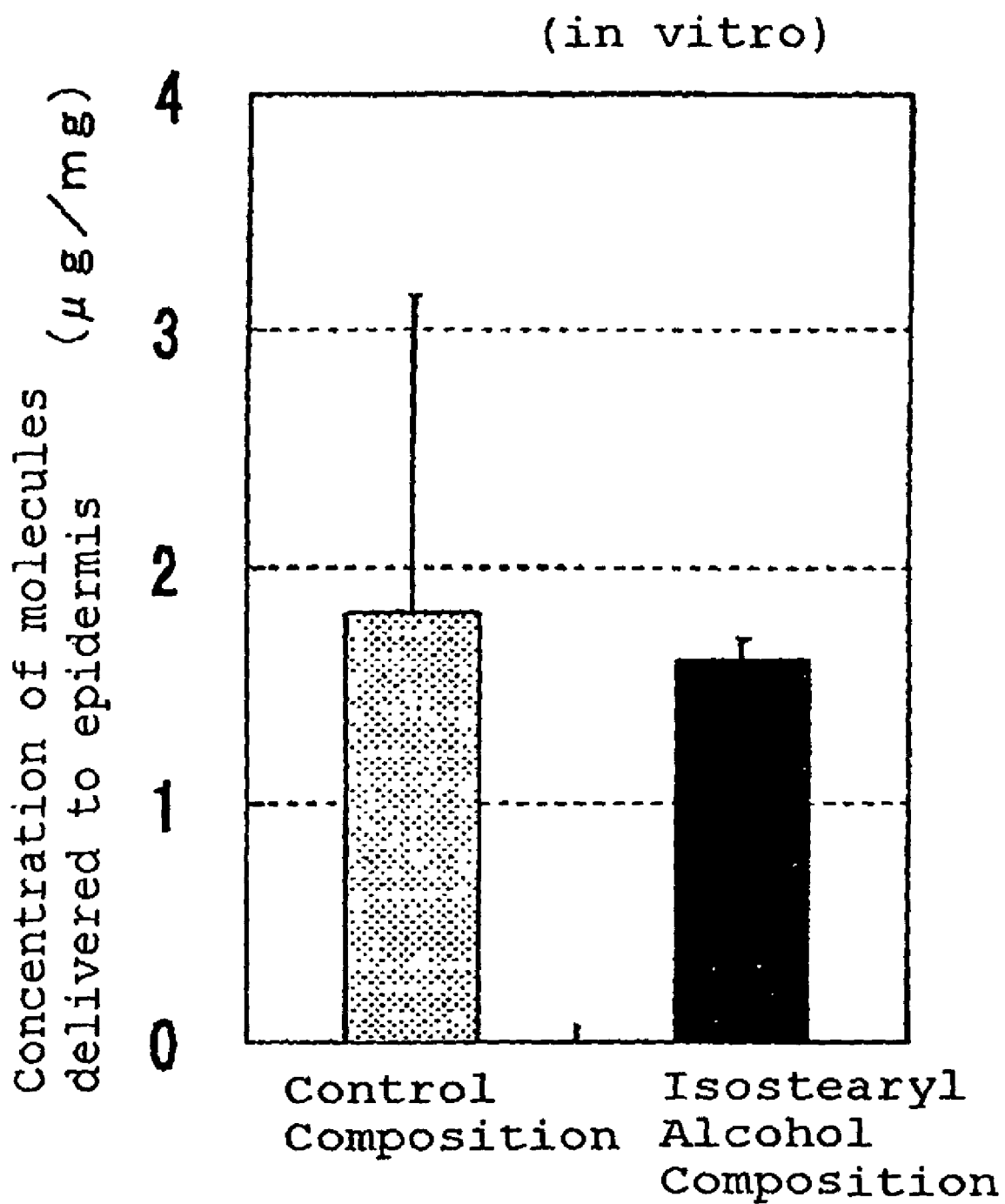
Figure 5C:
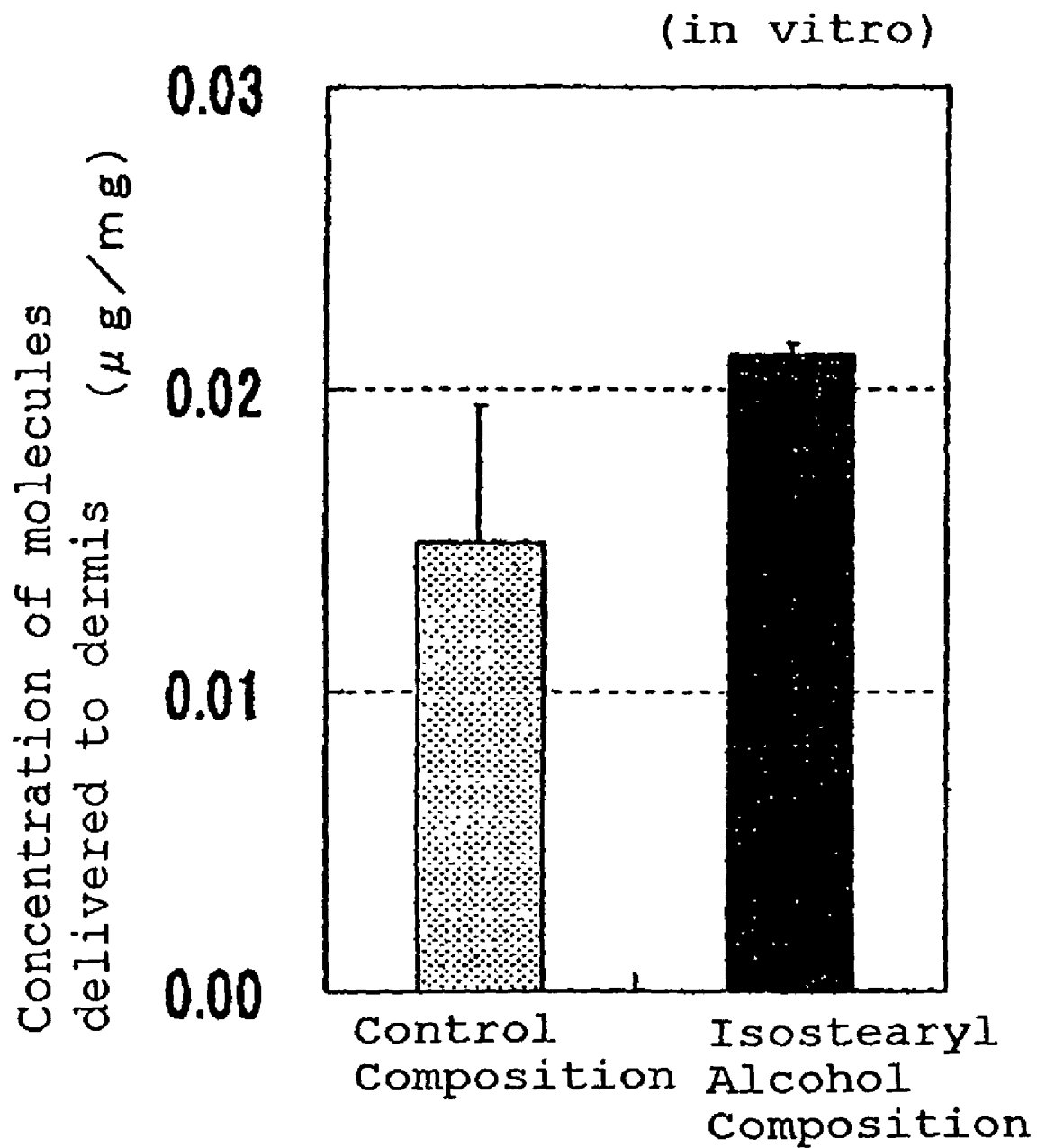

As is apparent from FIGS. 5A-5C, the concentration of pantothenyl ethylether delivered to the dermis is slightly increased in the presence of isostearyl alcohol. In contrast, the concentration of pantothenyl ethylether delivered to the stratum corneum or the epidermis is decreased in the presence of isostearyl alcohol. The results show that isostearyl alcohol specifically accelerates the skin-pore absorption of pantothenyl ethylether, but does not accelerate the transdermal absorption thereof.

In the test, it is shown that "skin-pore absorption" or "trans-follicular absorption" is an index of skin absorption different from "transdermal absorption", and in addition, that it is possible to measure skin absorption of a substance by regarding the result shown in FIG. 4 as a concentration of the substance delivered to hair follicles and regarding the results shown in FIGS. 5A-5C as concentrations of the substance delivered to other skin tissue of the skin of the miniature pig (stratum corneum, epidermis and dermis), and then using the resultant data as an index representing the amount of the substance which is absorbed through hair follicles and percutaneously.

(2) Ingredient Evaluation Test 2

Test samples comprising an oily ingredient having an I.O.B. value of 0.06-4.0 were prepared. Formulations of the respective samples are shown in Table 2.

TABLE 2

| Ingredient (wt. %) | Control composition | 1% Isostearyl alcohol composition |
| --- | --- | --- |
| Pantothenyl ethylether | 2.0 | 2.0 |
| 99% Ethanol | 88.0 | 87.0 |
| Ion-exchange water | 10.0 | 10.0 |
| Isostearyl alcohol | — | 1.0 |
| Benzyl alcohol | — | — |
| Isostearic acid | — | — |
| Lauric acid diethanolamide | — | — |
| Monoglyceryl isostearate | — | — |

| Ingredient (wt. %) | 1% Benzyl alcohol composition | 1% Isostearic acid composition |
| --- | --- | --- |
| Pantothenyl ethylether | 2.0 | 2.0 |
| 99% Ethanol | 87.0 | 87.0 |
| Ion-exchange water | 10.0 | 10.0 |
| Isostearyl alcohol | — | — |
| Benzyl alcohol | 1.0 | — |
| Isostearic acid | — | 1.0 |
| Lauric acid diethanolamide | — | — |
| Monoglyceryl isostearate | — | — |

| Ingredient (wt. %) | 1% Lauric acid diethanolamide composition | 1% monoglyceryl isostearate composition |
| --- | --- | --- |
| Pantothenyl ethylether | 2.0 | 2.0 |
| 99% Ethanol | 87.0 | 87.0 |
| Ion-exchange water | 10.0 | 10.0 |
| Isostearyl alcohol | — | — |
| Benzyl alcohol | — | — |
| Isostearic acid | — | — |
| Lauric acid diethanolamide | 1.0 | — |
| Monoglyceryl isostearate | — | 1.0 |

Figure 6:
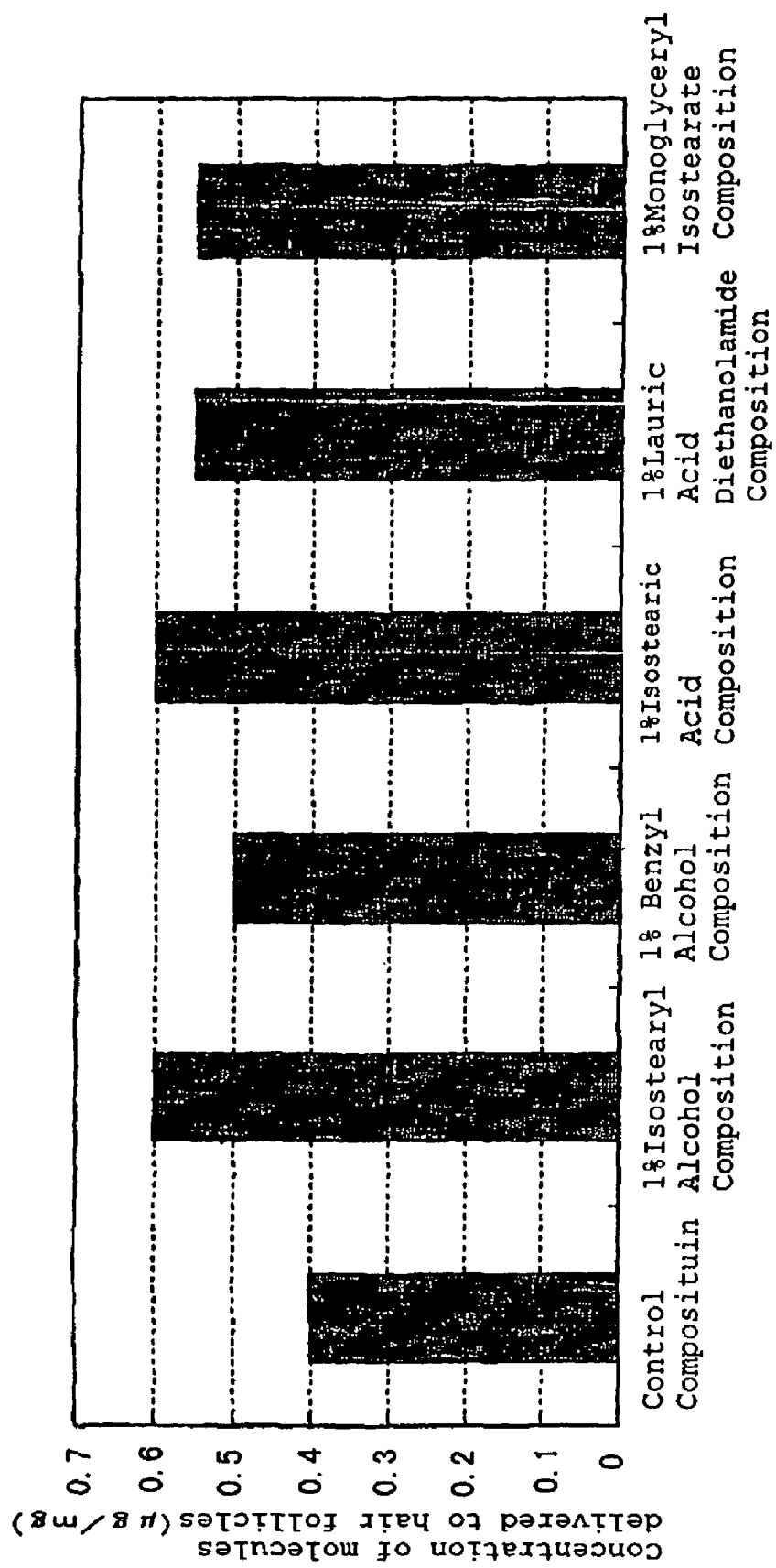
FIG. 6 shows the results of the evaluation of the effects of oily ingredients having I.O.B. values of 0.06-4.0 for accelerating the skin-pore absorption of pantothenyl ethylether.
Figure 7A:
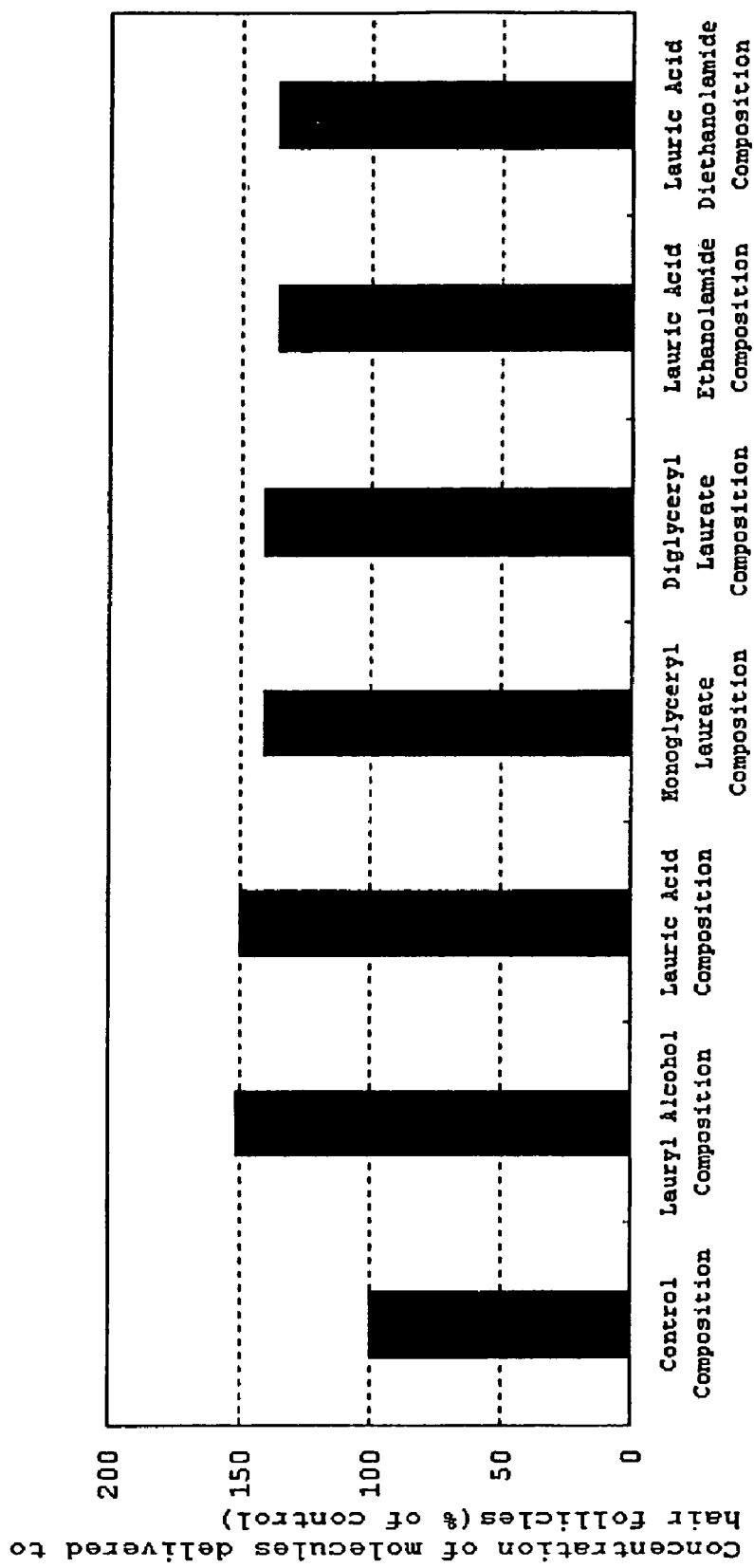
FIGS. 7A to 7D show the results of evaluation of the effects of other oily ingredients having I.O.B. values of 0.06-4.0 for accelerating the skin-pore absorption of pantothenyl ethylether.
Figure 7B:
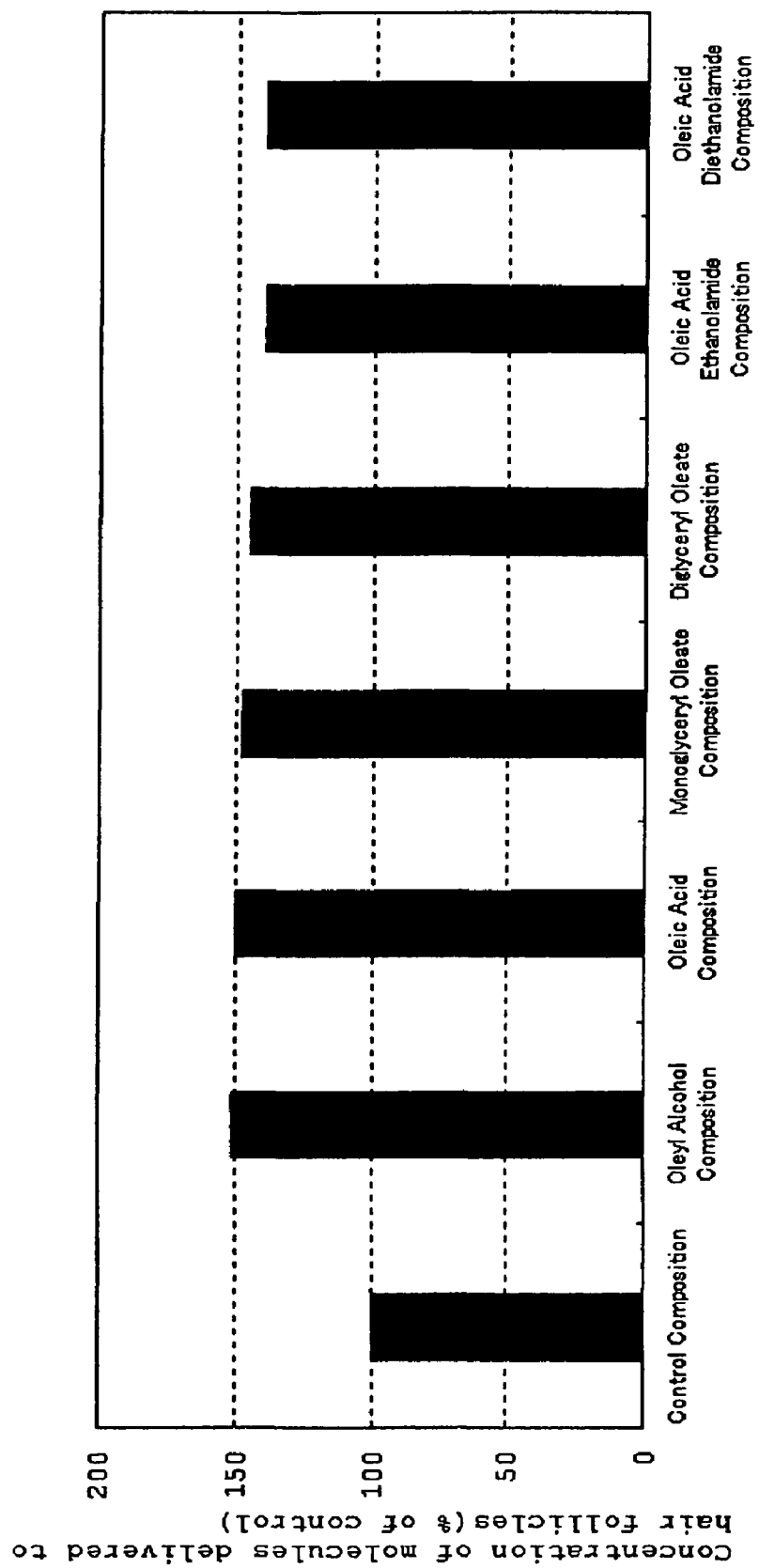
Figure 7C:
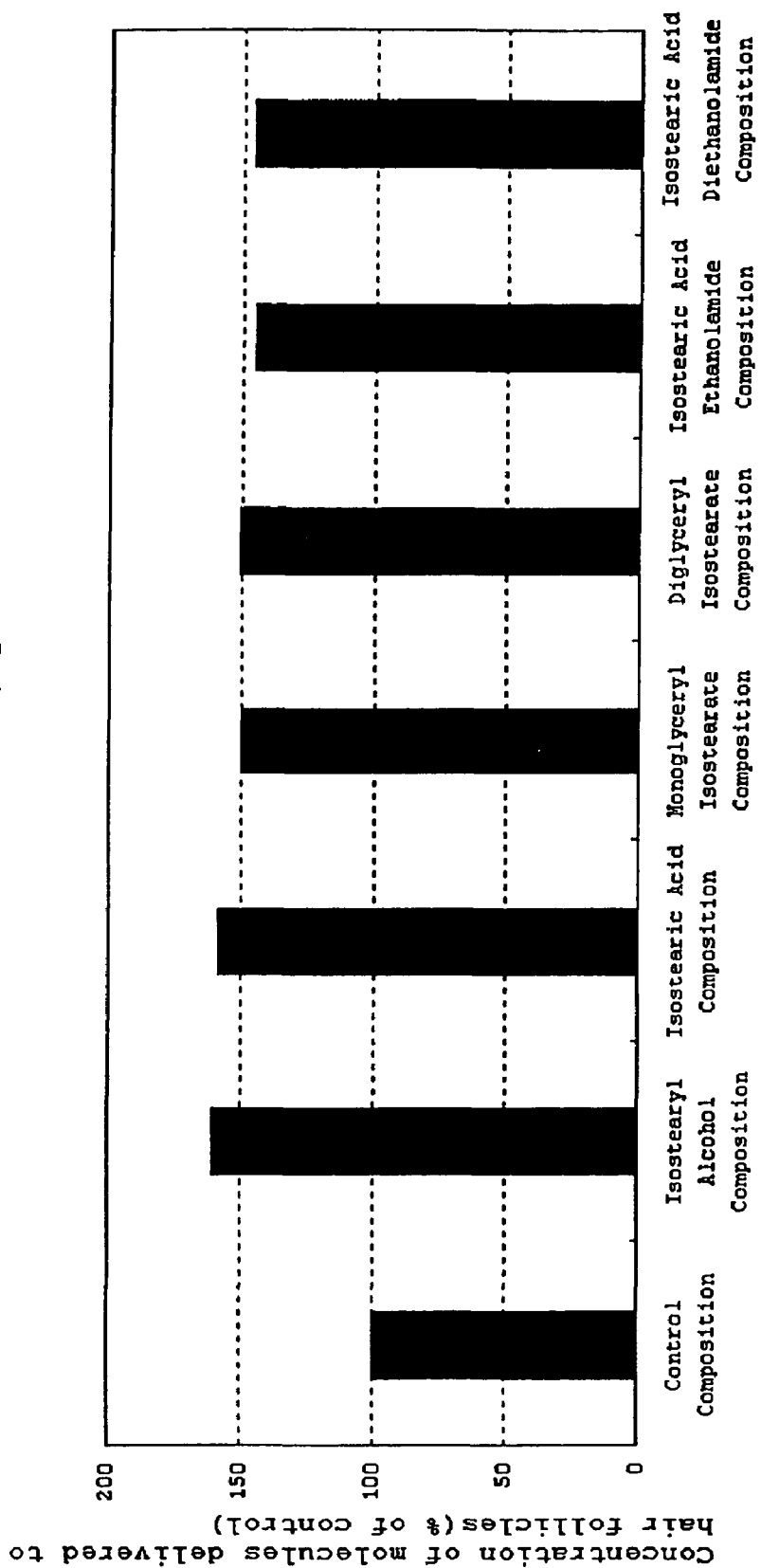
Figure 7D:
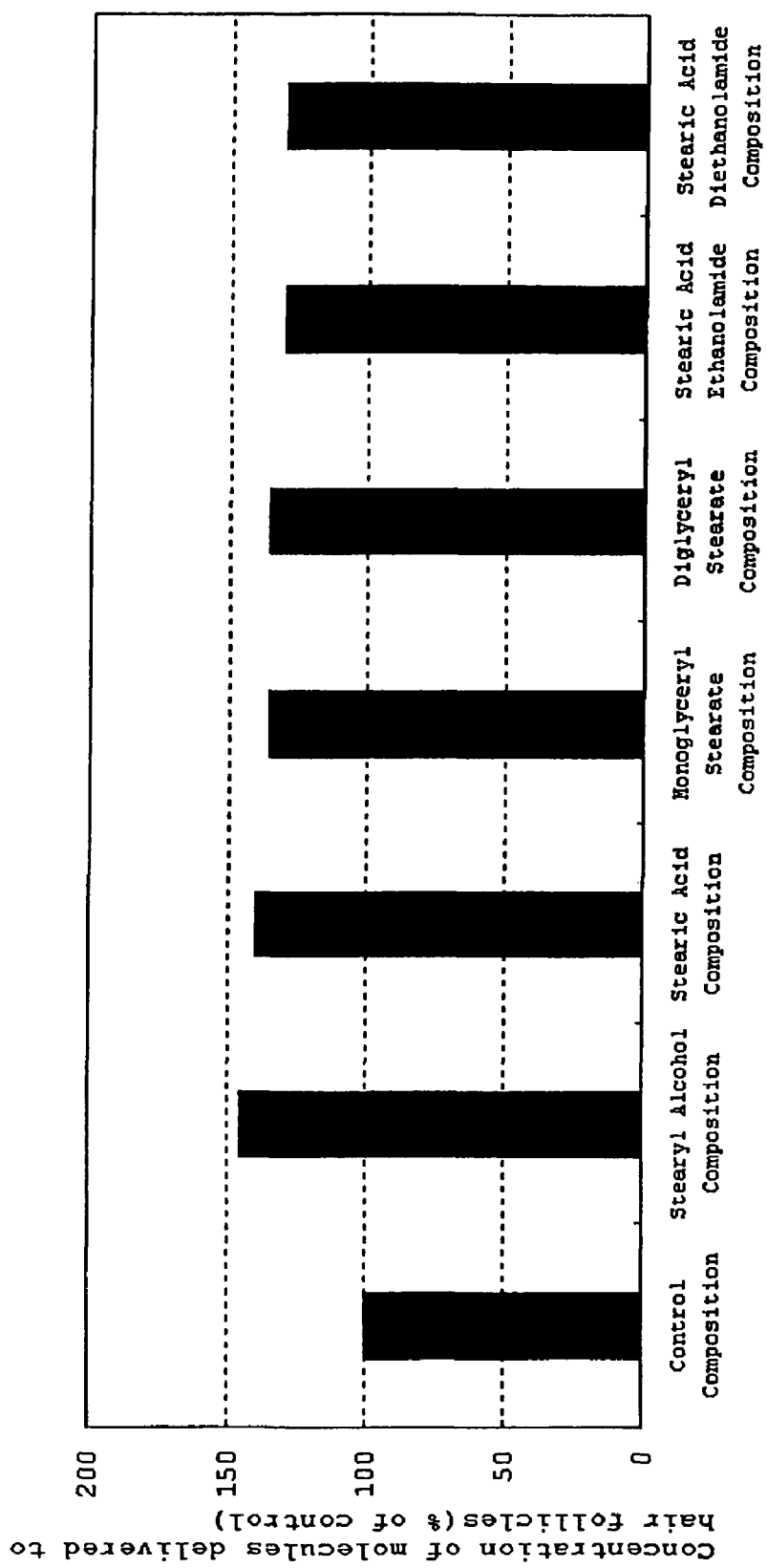

In each of six test samples, the concentration of pantothenyl ethylether which was delivered to the hair follicles was measured in a manner similar to that of the above accuracy test. Skin samples were derived from the upper back and lower back of the miniature pig (n=5). The results of the evaluation test are shown in FIG. 6. As is apparent from FIG. 6, in comparison with the control composition, in the compositions containing the oily ingredient having an I.O.B value of 0.06-4.0, the concentration of pantothenyl ethylether delivered to hair follicles increases. Particularly, in the isostearyl alcohol-containing composition and isostearic acid-containing composition, the concentration of pantothenyl ethylether delivered to hair follicles increases.

(3) Ingredient Evaluation Test 3

Test samples comprising an oily ingredient having an I.O.B. value of 0.06-4.0 were prepared. The oily ingredient was chosen from among lauryl alcohol, lauric acid, lauric acid ethanolamide, lauric acid diethanolamide, monoglyceryl laurate, diglyceryl laurate, oleyl alcohol, oleic acid, oleic acid ethanolamide, oleic acid diethanolamide, monoglyceryl oleate, diglyceryl oleate, isostearyl alcohol, isostearic acid, isostearic acid ethanolamide, isostearic acid diethanolamide, monoglyceryl isostearate, diglyceryl isostearate, stearyl alcohol, stearic acid, stearic acid ethanolamide, stearic acid diethanolamide, monoglyceryl stearate, and diglyceryl stearate. Each of these was incorporated into each test sample. Each of the test samples was prepared in a manner similar to that of ingredient evaluation test 2. The control composition employed in ingredient evaluation test 3 was the same as that employed in Test 2. Each of the test samples comprised 99% ethanol and the oily ingredient in amounts of 87% and 1%, respectively.

In each of the 24 test samples, the amount of pantothenyl ethylether which was absorbed through skin pores was measured in a manner similar to that of the above accuracy test. Skin samples were prepared from the miniature pig's upper back and lower back (n=5). The results of the evaluation test are shown in FIGS. 7A-7D. As is apparent from FIGS. 7A-7D, in comparison with the control composition, in the compositions containing the oily ingredient having an I.O.B value of 0.06-4.0, the concentration of pantothenyl ethyl ether delivered to hair follicles increases.

Measurement Method 1-2

In order to confirm the validity of the results of the tests by means of measurement method 1-1, the effect of isostearyl alcohol on accelerating skin-pore absorption was evaluated by means of measurement method 1-2 using human hair.

Thirty male panelists were enrolled in the test. Test samples (a control composition and a 5% isostearyl alcohol-containing composition) were prepared as shown in Table 1, except that the amount of pantothenyl ethylether was changed to 1%. Each of the test samples (0.5 ml for each) was applied to the scalp (area: 1 cm$^2$) of each male panelist, and then the scalp was left for 16 hours. After the scalp had been washed, 20 hair fibers were plucked from the scalp of each panelist, to which the test sample had been applied. The hair roots were cut off the hair fibers, and the concentration of pantothenyl ethylether delivered to the hair shafts and outer root sheaths of the hair roots of the 20 hair fibers was measured by means of liquid chromatography under the same conditions as described above.

Figure 8:
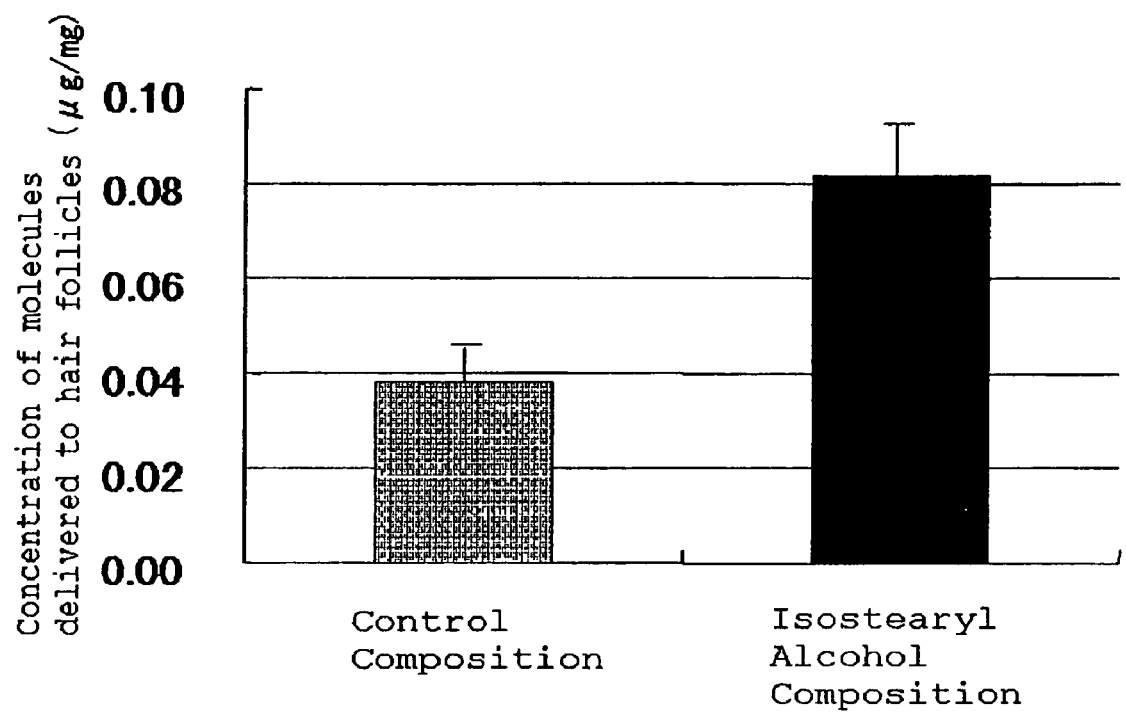
FIG. 8 shows the results of the evaluation test conducted by means of measurement method 1-2.

The results of the test are shown in FIG. 8.

The results obtained through measurement method 1-2 also show that the concentration of pantothenyl ethylether delivered to the hair follicles increases in the presence of isostearyl alcohol; i.e., isostearyl alcohol accelerates the skin-pore absorption of pantothenyl ethylether.

3. Test for Comparison of Isostearyl Alcohol and Transdermal Absorption-Accelerating Agent The test was carried out by means of measurement method 1-1 using a specific amine oxide known as a transdermal absorption-accelerating agent for comparison.

In the comparison test, the procedure of the above-described test by means of measurement method 1-1 was repeated, except that different test samples were employed and that the concentrations of β-glycyrrhetinic acid and minoxidil delivered to the hair follicles were measured by means of liquid chromatography (under the same conditions as described above). Formulations of the respective test samples are shown in Table 3.

TABLE 3

|  | Control composition | Isostearyl alcohol composition | Amine oxide composition |
|---|---|---|---|
| Minoxidil | 0.5 | 0.5 | 0.5 |
| β-Glycyrrhetinic acid | 0.5 | 0.5 | 0.5 |
| Ethanol | 75 | 70 | 70 |
| Ion-exchange water | 22.91 | 22.91 | 22.91 |
| Isostearyl alcohol | — | 5 | — |
| Lauryl dimethylamine oxide | — | — | 5 |
| Sodium oleate | 0.1 | 0.1 | 0.1 |
| Sodium dodecylbenzenesulfonate | 0.49 | 0.49 | 0.49 |
| Polyoxyethylene hydrogenated castor oil (40 E.O.) | 0.5 | 0.5 | 0.5 |
| Total | 100 | 100 | 100 |

Figure 9A:
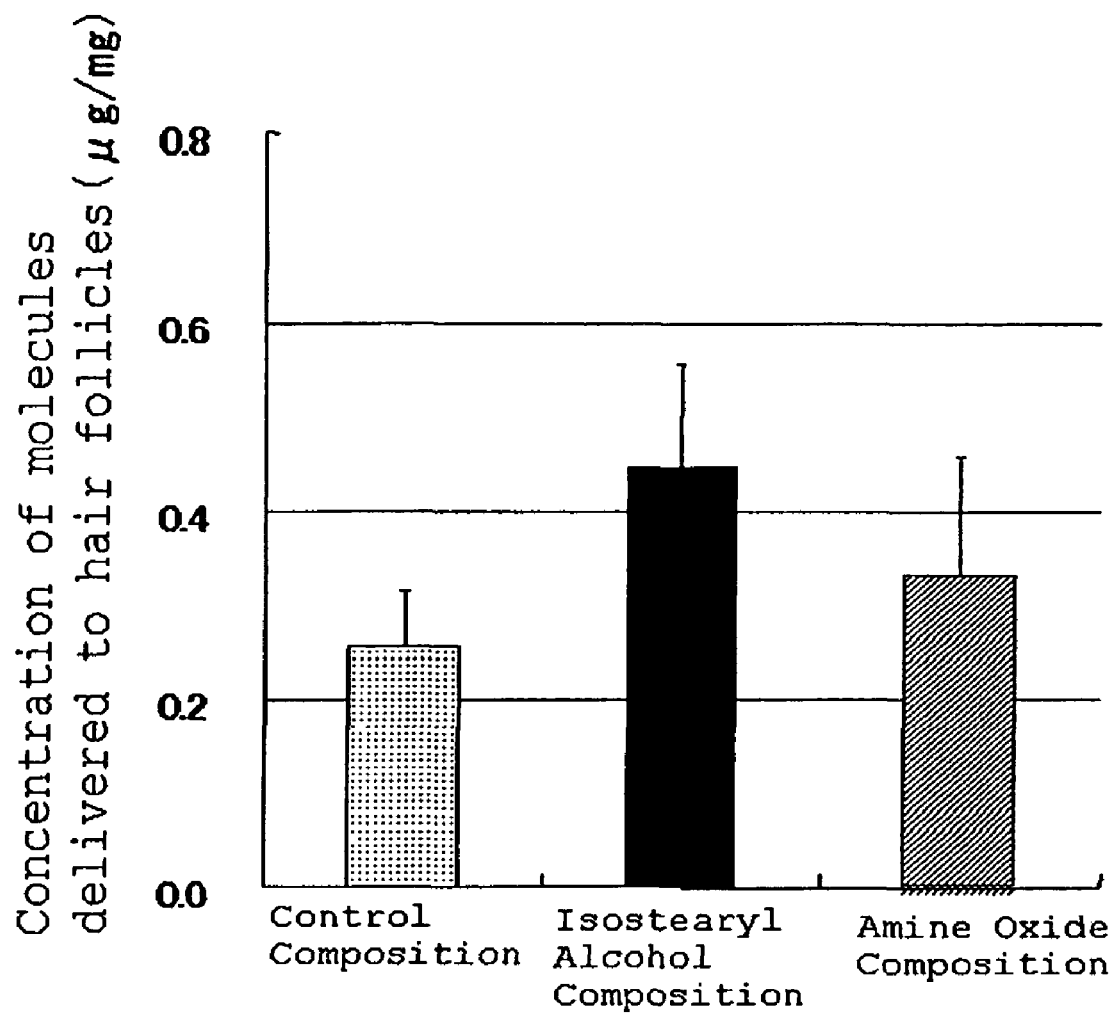
FIGS. 9A and 9B show the results of a comparison between isostearyl alcohol and a transdermal absorption-accelerating agent.
Figure 9B:
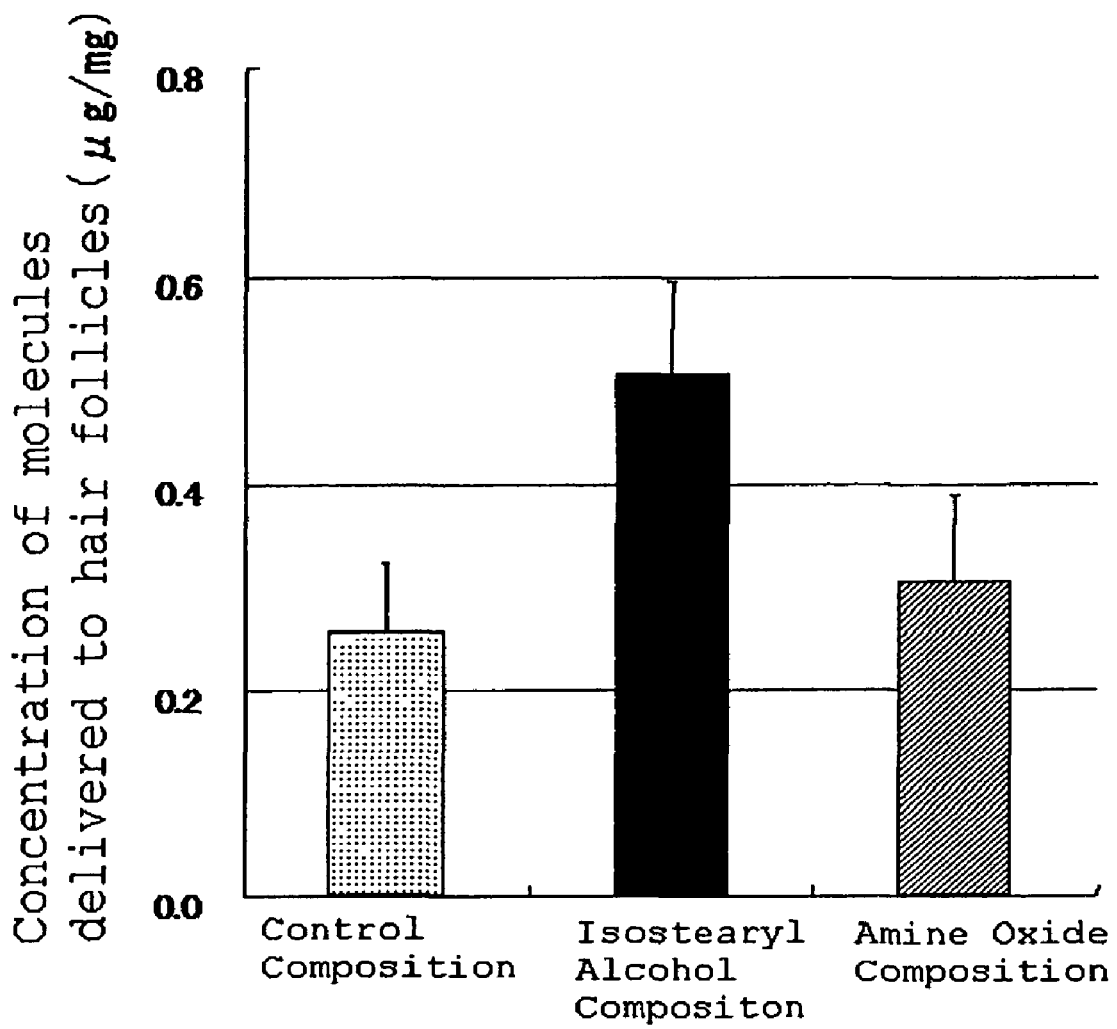

The results of the test are shown in FIGS. 9A and 9B. FIG. 9A shows the concentration of β-glycyrrhetinic acid delivered to the hair follicles, and FIG. 9B shows the concentration of minoxidil delivered to the hair follicles. The results clearly show that isostearyl alcohol accelerates the skin-pore absorption of active ingredients (β-glycyrrhetinic acid and minoxidil) as compared with amine oxide, and that skin-pore absorption has different mechanism from transdermal absorption.

4. Test for Evaluation of Refreshing Agent

The test was carried out using test samples containing various terpene compounds known to be refreshing agents. The procedure of the above-described test by means of measurement method 1-2 was repeated, except that the test samples containing terpene compounds were employed. Formulations of the respective test samples are shown in Table 4.

TABLE 4

|  | Control composition | Camphor composition | Menthol composition | Eucalyptus oil composition |
|---|---|---|---|---|
| Pantothenyl ethylether | 0.5 | 0.5 | 0.5 | 0.5 |
| Ethanol | 71 | 70 | 70 | 70 |
| Ion-exchange water | 28.5 | 28.5 | 28.5 | 28.5 |
| Camphor | — | 1 | — | — |
| Menthol | — | — | 1 | — |
| Eucalyptus oil | — | — | — | 1 |
| Total | 100 | 100 | 100 | 100 |

Figure 10:
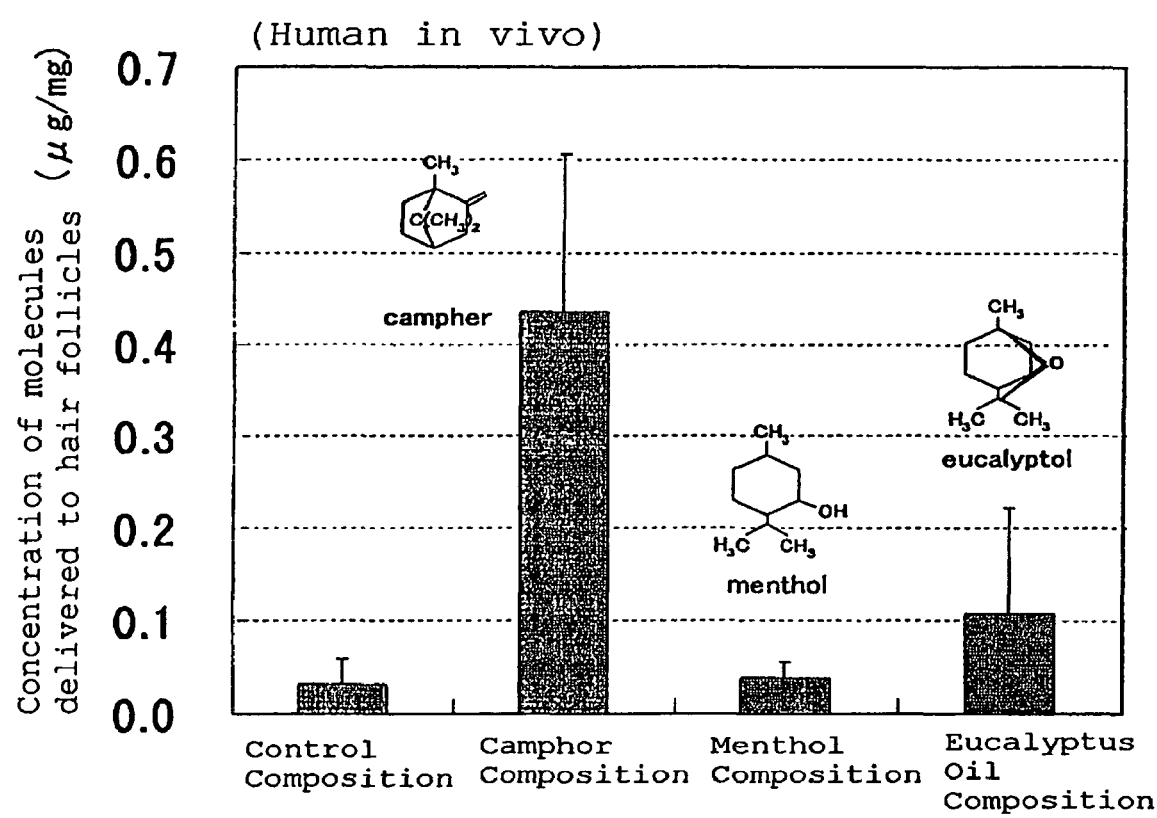
FIG. 10 shows the results of the evaluation of refreshing agents conducted by means of measurement method 1-2.

The results of the test are shown in FIG. 10. The results show that only camphor accelerates the skin-pore absorption of pantothenyl ethylether.

Figure 11B:
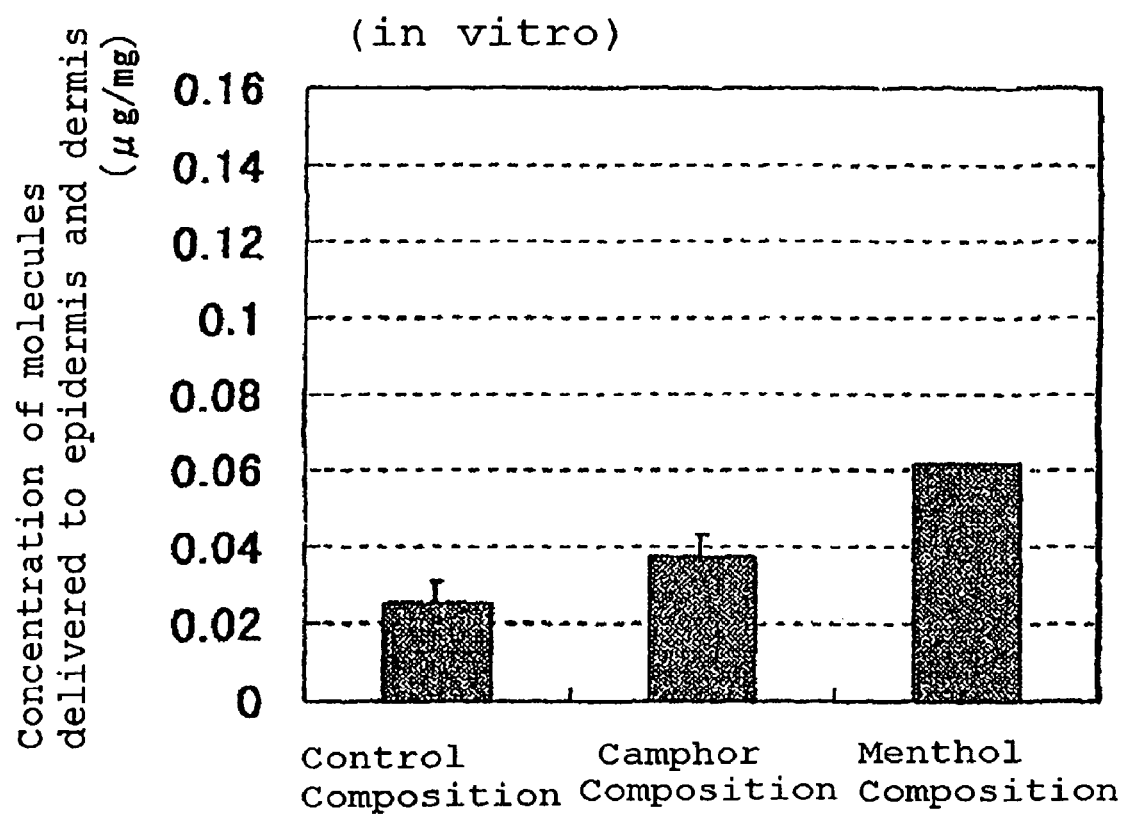

The procedure of the above-described test by means of measurement method 1-1 was repeated, except that the test samples containing terpene compounds were employed. The results are shown in FIGS. 11A and 11B. FIG. 11A shows the concentration of pantothenyl ethylether delivered to the hair follicles, and FIG. 11B shows the concentration of pantothenyl ethylether delivered to the epidermis and the dermis. As is apparent from FIGS. 11A and 11B, only camphor accelerates the skin-pore absorption of pantothenyl ethylether.

Measurement Method 2

The sebum transferability of a minoxidil-containing composition was evaluated by use of the kit 10 of the present invention.

1. Minoxidil-containing compositions (minoxidil content: 2%) were prepared, and each of the compositions (20 µl) was employed in the test. Formulations of the respective compositions are shown in Table 5.

TABLE 5

|  | Ethanol | Dipropylene glycol | C8 monoglyceride | Ethyl lactate | Cetostearyl alcohol | Isostearyl alcohol |
|---|---|---|---|---|---|---|
| 99% Alcohol | 88 | 38 | 82.7 | 82.7 | 82.7 | 82.7 |
| Polyoxyethylene hydrogenated castor oil (60 E.O.) | — | — | 0.1 | 0.1 | 0.1 | 0.1 |
| Isostearic acid | — | — | 0.2 | 0.2 | 0.2 | 0.2 |
| Ion-exchange water | 10 | 10 | 10 | 10 | 10 | 10 |
| Dipropylene glycol | — | 50 | — | — | — | — |
| Propylene glycol | — | — | — | — | — | — |
| Isostearyl alcohol | — | — | — | — | — | 5 |
| Cetostearyl alcohol | — | — | — | — | 5 | — |
| Ethyl lactate | — | — | — | 5 | — | — |
| C8 monoglyceride | — | — | 5 | — | — | — |
| Minoxidil | 2 | 2 | 2 | 2 | 2 | 2 |
| Total | 100 | 100 | 100 | 100 | 100 | 100 |

2. Artificial sebum was prepared. The formulation of the artificial sebum is as follows.

| Ingredient | Amount (wt. %) |
|---|---|
| Triolein | 40.0 |
| Palmitoleic acid | 26.0 |
| Wax ester | 20.0 |
| Squalane | 10.0 |
| Palmitic acid | 2.0 |
| Cholesterol | 2.0 |
|  | 100.0 |

The thus-prepared artificial sebum (11.5 ml) was placed in the sealable receptacle 11.

3. A Franz cell (volume: 11.5 ml) was employed as the receptacle 11, and a syringe was employed for collecting the artificial sebum from the cell.

4. A single-layer silicone film, one surface of which was subjected to keratinization, was employed as the thin film 12.

The test was carried out under the aforementioned conditions. Specifically, each of the compositions (20 µl) was applied on the thin film, and the resultant film was allowed to stand at 37° C. for 24 hours. The degree of transfer of minoxidil to the artificial sebum was evaluated on the basis of the concentration of minoxidil contained in the sebum after the elapse of a specified time period.

Figure 12:
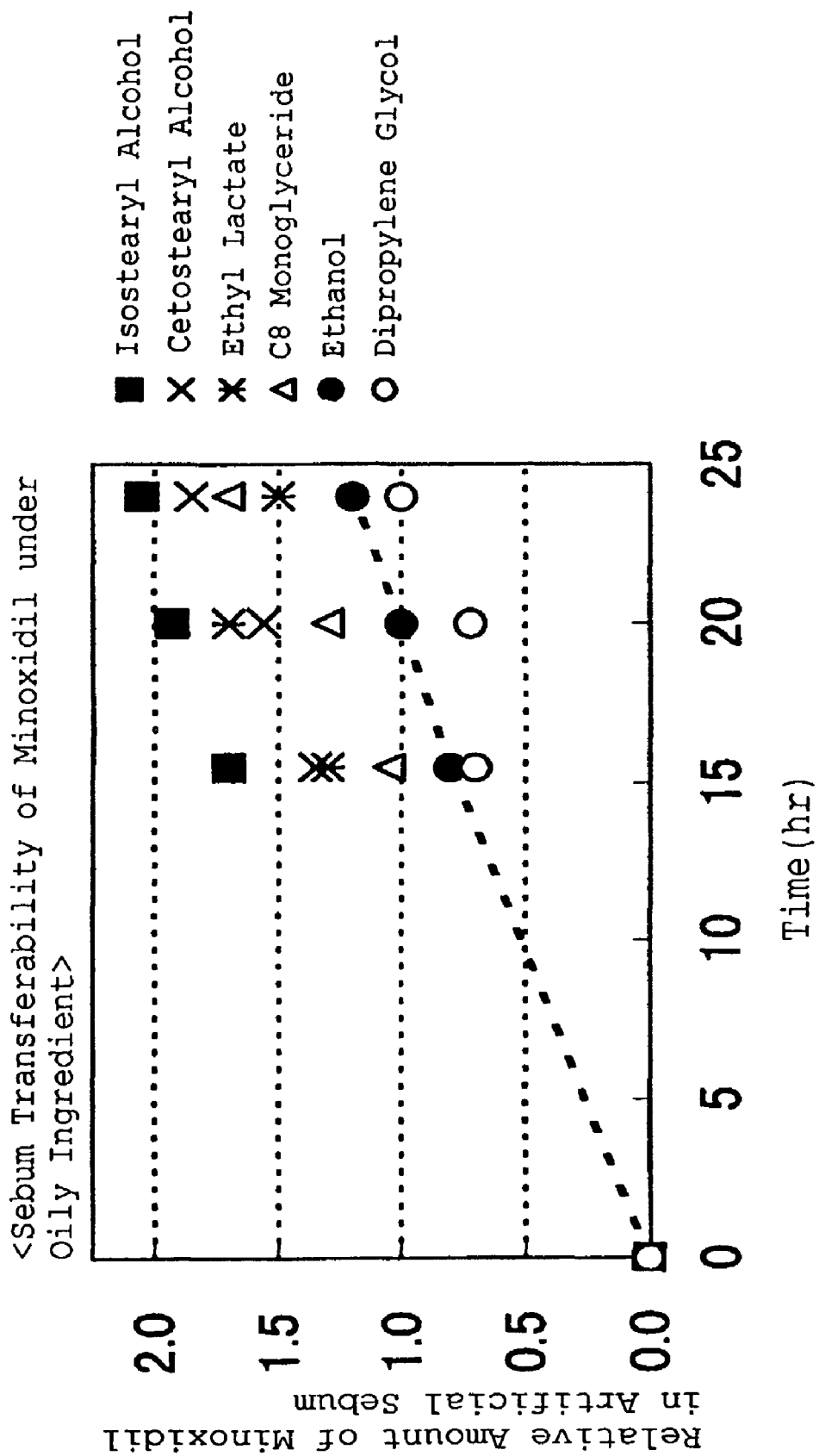
FIG. 12 shows the results of the test in which measurement method 2 is carried out by use of the kit of the present invention.

The concentration of minoxidil in the artificial sebum was measured at predetermined points in time by the following procedure. The artificial sebum (0.5 ml) was collected by use of a syringe equipped with a needle, and the collected sebum was stirred. After completion of stirring, methanol (1.0 ml) was added to the sebum, and the resultant mixture was allowed to stand, and then the mixture was subjected to centrifugation at 4,000 rpm for five minutes. Subsequently, the methanol solution (0.5 ml) which was separated from the mixture through the centrifugation was collected, and then the solution was diluted with methanol (1 ml). The thus-diluted solution was employed as a sample. The sample was subjected to high-performance liquid chromatography (Nanospace (product of Shiseido Co., Ltd.), column: Capsule Pack C18, eluent: ($CH_3CN:H_2O$=20:80)), to thereby quantify the concentration of minoxidil. The results are shown in FIG. 12.

The results show that isostearyl alcohol enhances the sebum transferability of minoxidil.

4. Formulation Examples of the Composition of the Present Invention

Typical formulation examples of the composition of the present invention are described below. The below-described formulations are prepared through customary methods.

| Ingredient | Amount (wt. %) |
|---|---|
| (Formulation 1) Hair-growing agent | |
| Pantothenyl ethylether | 0.5 |
| β-glycyrrhetinic acid | 0.5 |
| Swertia herb extract paste | 0.5 |
| Nicotinamide | 0.5 |
| Vitamin E acetate | 0.5 |
| Ethanol | 70.0 |
| Ion-exchange water | 21.41 |
| Isostearyl alcohol | 5.0 |
| Sodium lauryldimethylamine oxide oleate | 0.49 |
| Polyoxyethylene hydrogenated castor oil (40 E.O.) | 0.5 |

| Ingredient | Amount (wt. %) |
|---|---|
| (Formulation 2) Shampoo | |
| Sodium cocoyl methyl taurate | 10.0 |
| Cocamide propyl betaine | 5.0 |
| Glycerin | 1.0 |
| Citric acid | 1.0 |
| Isostearyl alcohol | 5.0 |
| Taurine | 1.5 |
| Methyltaurine | 0.5 |
| Cationized cellulose | 0.5 |
| Perfume | suitable amount |
| Ion-exchange water | balance |
| (Formulation 3) Rinse-treatment | |
| Stearyltrimethylammonium chloride | 1.0 |
| Isostearyl alcohol | 3.0 |
| Palmitic acid | 1.0 |
| L-Glutamine | 0.1 |
| Ion-exchange water | balance |
| (Formulation 4) Conditioning shampoo | |
| Sodium N-cocoyl-N-methyl taurate | 7.0 |
| Cocamide propyl betaine | 7.0 |
| N-[3-(Dimethylamino)propyl]octadecanamide | 0.1 |
| Isostearyl alcohol | 0.25 |
| Ion-exchange water | balance |
| (Formulation 5) Gray-hair prevention agent | |
| 95% Ethanol | 55.0 |
| Japanese pepper extract | 5.0 |
| Nicotinamide | 0.5 |
| Hinokitiol | 0.2 |
| 1,3-Butylene glycol | 1.5 |
| Polyoxyethylene hydrogenated castor oil (60 E.O.) | 1.0 |
| Isostearyl alcohol | 5.0 |
| Succinic acid | suitable amount |
| Perfume | suitable amount |
| Coloring agent | suitable amount |
| Ion-exchange water | balance |
| (Formulation 6) Hair-removing agent | |
| 95% Ethanol | 55.0 |
| Calcium thioglycolate | 5.0 |
| 1,3-Buthylene glycol | 1.5 |
| Polyoxyethylene hydrogenated castor oil (60 E.O.) | 1.0 |
| Isostearyl alcohol | 5.0 |
| Succinic acid | suitable amount |
| Perfume | suitable amount |
| Coloring agent | suitable amount |

What is claimed is:

1. A method for accelerating skin-pore absorption of a substance having skin-pore absorbability comprising:
   mixing the substance having skin-pore absorbability with isostearyl alcohol to form a mixture, said substance having skin-pore absorbability being pantothenyl ethylether or β-glycyrrhetinic acid, and
   applying the mixture to the skin.

* * * * *